US011267879B2

(12) United States Patent
Geng et al.

(10) Patent No.: US 11,267,879 B2
(45) Date of Patent: *Mar. 8, 2022

(54) COMPOSITIONS, DEVICES, KITS AND METHODS FOR DETECTING HOOKWORM

(71) Applicant: IDEXX Laboratories, Inc., Westbrook, ME (US)

(72) Inventors: Jinming Geng, Scarborough, ME (US); David Allen Elsemore, South Portland, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/823,942

(22) Filed: Mar. 19, 2020

(65) Prior Publication Data

US 2020/0239558 A1  Jul. 30, 2020

Related U.S. Application Data

(60) Division of application No. 14/974,659, filed on Dec. 18, 2015, now Pat. No. 10,640,551, which is a division of application No. 12/467,778, filed on May 18, 2009, now Pat. No. 9,239,326, which is a continuation-in-part of application No. 11/763,583, filed on Jun. 15, 2007, now Pat. No. 9,063,129.

(60) Provisional application No. 61/122,254, filed on Dec. 12, 2008.

(51) Int. Cl.
*G01N 33/53* (2006.01)
*C07K 16/18* (2006.01)

(52) U.S. Cl.
CPC ......... *C07K 16/18* (2013.01); *G01N 33/5308* (2013.01); *G01N 2333/4353* (2013.01); *G01N 2333/43526* (2013.01)

(58) Field of Classification Search
None
See application file for complete search history.

(56) References Cited

U.S. PATENT DOCUMENTS

| | | | |
|---|---|---|---|
| 4,322,495 A | 3/1982 | Kato | |
| 4,756,908 A | 7/1988 | Lew | |
| 4,789,631 A | 12/1988 | Maggio | |
| 4,839,275 A | 6/1989 | Weil | |
| 4,978,504 A | 12/1990 | Nason | |
| 5,078,968 A | 1/1992 | Nason | |
| 5,238,649 A | 8/1993 | Nason | |
| 5,266,266 A | 11/1993 | Nason | |
| 5,726,010 A | 3/1998 | Clark | |
| 5,753,787 A | 5/1998 | Hawdon et al. | |
| 5,843,706 A | 12/1998 | Cobon et al. | |
| 5,882,943 A | 3/1999 | Aldeen | |
| 6,057,166 A | 5/2000 | Childs et al. | |
| 6,391,569 B1 | 5/2002 | Grieve et al. | |
| 6,596,502 B2 | 7/2003 | Lee | |
| 7,303,752 B2 | 12/2007 | Hotez et al. | |
| 7,736,660 B2 | 6/2010 | Elsemore et al. | |
| 7,951,547 B2 * | 5/2011 | Elsemore | G01N 33/5308 435/7.1 |
| 7,993,861 B2 | 8/2011 | Elsemore et al. | |
| 7,993,862 B2 | 8/2011 | Elsemore et al. | |
| 8,097,261 B2 | 1/2012 | Elsemore et al. | |
| 8,105,795 B2 | 1/2012 | Elsemore et al. | |
| 8,268,574 B2 | 9/2012 | Elsemore et al. | |
| 8,367,808 B2 | 2/2013 | Elsemore et al. | |
| 8,580,518 B2 | 11/2013 | Elsemore et al. | |
| 8,895,294 B2 * | 11/2014 | Elsemore | G01N 33/6893 435/287.1 |
| 9,040,245 B2 * | 5/2015 | Elsemore | G01N 33/6893 435/7.1 |
| 9,063,129 B2 | 6/2015 | Elsemore et al. | |
| 9,103,823 B2 | 8/2015 | Elsemore et al. | |
| 9,212,220 B2 | 12/2015 | Elsemore et al. | |
| 9,239,326 B2 * | 1/2016 | Geng | G01N 33/5308 |
| 9,746,469 B2 * | 8/2017 | Elsemore | G01N 33/56966 |
| 10,429,388 B2 * | 10/2019 | Elsemore | G01N 33/6893 |
| 10,640,551 B2 * | 5/2020 | Geng | G01N 33/5308 |

(Continued)

FOREIGN PATENT DOCUMENTS

| WO | WO 98/12563 | 3/1998 |
|---|---|---|
| WO | WO 2002/075313 | 9/2002 |

(Continued)

OTHER PUBLICATIONS

Bethany et al, The Lancet, May 6, 2006, 367:1521-1532. (Year: 2006).*
Coulaud et al, Acta Tropica, 1984, 41:87-90 (Year: 1984).*
Australian Government, Anthelmintics for dogs and cats | Australian Pesticides and Veterinary medicines Authority. Jul. 1, 2014, 3 pages, https://apvma.gov.au/node/917 (Year: 2014).*
Interceptor for Animal Use—Drugs.com, https://www.drugs.com/vet/interceptor.html, 9 pages. 2020 (Year: 2020).*
Interceptor Plus for Animal Use—Drugs.com, https://www.drugs.com/vet/interceptor-plus.html 9 pages. 2019 (Year: 2019).*
Hess et al, Journal of the American Animal Hospital Association, (May/Jun. 2019) vol. 55, No. 3, pp. 160-166. Electronic Publication Date: Mar. 14, 2019 (Year: 2019).*
Becker et al, Parasitol Res (2012) 111:849-857. Published online: Apr. 13, 2012 (Year: 2012).*

(Continued)

*Primary Examiner* — Nita M. Minnifield
(74) *Attorney, Agent, or Firm* — McDonnell Boehnen Hulbert & Berghoff LLP

(57) ABSTRACT

Methods, devices, kits and compositions for detecting the presence or absence of hookworm in a fecal sample are disclosed herein. The methods, devices, kits and compositions of the present invention may be used to confirm the presence or absence of hookworm in a fecal sample from a mammal that may also be infected with one or more of roundworm, whipworm, and heartworm. Confirmation of the presence or absence of hookworm in the mammal may be made, for example, for the purpose of selecting an optimal course of treating the mammal and/or for the purpose of determining whether the mammal has been rid of the infection after treatment has been initiated.

12 Claims, 6 Drawing Sheets

Specification includes a Sequence Listing.

(56) References Cited

U.S. PATENT DOCUMENTS

| | | | |
|---|---|---|---|
| 10,942,180 B2* | 3/2021 | Elsemore | G01N 33/56966 |
| 11,001,626 B2* | 5/2021 | Geng | G01N 33/5308 |
| 2002/0132270 A1 | 9/2002 | Lee | |
| 2003/0129680 A1 | 7/2003 | O'Connor | |
| 2004/0014087 A1 | 1/2004 | Hodgson et al. | |
| 2004/0214244 A1 | 10/2004 | Tonelli et al. | |
| 2005/0042232 A1 | 2/2005 | Hotez et al. | |
| 2006/0198844 A1 | 9/2006 | Langenfeld | |
| 2007/0053920 A1 | 3/2007 | Heath et al. | |
| 2008/0033148 A1 | 2/2008 | Xu et al. | |
| 2008/0108793 A1 | 5/2008 | Berman et al. | |
| 2008/0311557 A1 | 12/2008 | Elsemore et al. | |
| 2008/0311600 A1 | 12/2008 | Elsemore et al. | |
| 2009/0286227 A1 | 11/2009 | Elsemore et al. | |
| 2009/0286228 A1 | 11/2009 | Elsemore et al. | |
| 2009/0286229 A1 | 11/2009 | Elsemore et al. | |
| 2009/0286230 A1 | 11/2009 | Elsemore et al. | |
| 2009/0286231 A1* | 11/2009 | Elsemore | G01N 33/5308 435/5 |
| 2010/0151500 A1* | 6/2010 | Geng | G01N 33/5308 435/7.22 |
| 2013/0149694 A1* | 6/2013 | Elsemore | G01N 33/6893 435/5 |
| 2014/0205994 A1* | 7/2014 | Elsemore | G01N 33/6893 435/5 |
| 2015/0260718 A1* | 9/2015 | Elsemore | G01N 33/6893 506/18 |
| 2016/0145327 A1* | 5/2016 | Geng | C07K 16/18 435/7.93 |
| 2017/0343544 A1 | 11/2017 | Elsemore et al. | |
| 2018/0149650 A1* | 5/2018 | Elsemore | G01N 33/56966 |
| 2019/0376967 A1* | 12/2019 | Elsemore | G01N 33/5308 |
| 2020/0102378 A1* | 4/2020 | Geng | G01N 33/563 |
| 2020/0239558 A1* | 7/2020 | Geng | G01N 33/5308 |
| 2021/0164980 A1* | 6/2021 | Elsemore | G01N 33/6893 |
| 2021/0324055 A1* | 10/2021 | Geng | G01N 33/5308 |

FOREIGN PATENT DOCUMENTS

| | | |
|---|---|---|
| WO | WO 2003/032917 | 4/2003 |
| WO | WO 2004/097412 | 11/2004 |
| WO | WO 2006/135799 | 12/2006 |
| WO | WO 2008/156650 | 12/2008 |
| WO | WO 2009/143080 | 11/2009 |
| WO | WO 2009/143083 | 11/2009 |

OTHER PUBLICATIONS

Catton et all Parasitol Res., 2003, 90:S144-S145 (Year: 2003).*
S.G. Drukovsky et al /J. Pharm. Sci. & Res. vol. 10(12), 2018, 3095-3098 (Year: 2018).*
Kopp et al, Veterinary Parasitology 152 (2008) 284-293 (Year: 2007).*
Kotze AC, Kopp SR (2008) The Potential Impact of Density Dependent Fecundity on the Use of the Faecal Egg Count Reduction Test for Detecting Drug Resistance in Human Hookworms. PLoS Negl Trap Dis 2(10): e297. 6 pages. published: Oct. 1, 2008 (Year: 2008).*
Payne et al. (J Am Vet Med Assoc 2002;220:330-333) Feb. 1, 2002 (Year: 2002).*
Rehbein et al Parasitol Res (2017) 116:259-269. Published online: Oct. 22, 2016 (Year: 2017).*
Rehbein et al. Veterinary Parasitology 202 (2014) 10-17. (Year: 2014).*
Rohdich et al. Parasites & Vectors (2018) 11:589. 7 pages. (Year: 2018).*
Sager et al, Parasitol Res (2006) 98: 333-338. Published online: Dec. 22, 2005 (Year: 2006).*
Schimmel et al, Parasitol Res (2009) 105:S9-S16. (Year: 2009).*
Six et al. Veterinary Parasitology 91 (2000) 321-331 (Year: 2000).*
Taweethavonsawat et al. Parasitol Res. (2010) 106:533-537. Published online: Nov. 13, 2009 (Year: 2009).*
Vercruysse et al. Veterinary Parasitology. 2002. 103:277-297. (Year: 2002).*
Vercruysse et al. Veterinary Parasitology, 2001. 96:171-193 (Year: 2001).*
Allan, et al., "Coproantigen detection for immunodiagnosis of echinococcosis and taeniasis in dogs and humans", *Parasitology*, 1992, 104:347-355.
Barker, et al., "Isolation of a gene family that encodes the porin-like proteins from the human parasitic nematode Trichuristrichiura", Gene, 1999, 229:131-136.
Bethony, et al., "Antibodies against a secreted protein from hookworm larvae reduce the intensity of hookworm infection in humans and vaccinated laboratory animals", *FASEB Journal*, 2005, 19:1743-1745.
Bungiro, et al., "Detection of excretory/secretory coporantigens in experimental hookworm infection", *Am. J. Trop. Med. Hyg.*, 2005, 73(5):915-920.
Bungiro, et al., "Purification and molecular cloning of and immunization with *Ancylostoma ceylanicum* excretory-secretory protein 2, an immunoreactive protein produced by adult hookworms", *Infection and Immunity*, 2004, 72(4):2203-2213.
Croese, et al., "Occult enteric infection by *Ancylostoma caninum*: A previously unrecognized zoonosis", *Gastroenterology*, 1994, 106:3-12.
Daub, et al., "A survey of genes expressed in adults of the human hookworm, *Nacator americanus*", *Parasitology*, 2000, 120:171-184.
De Oliveira Vasconcelos, et al., "Identification of stage-specific proteins of Angiostrongylus vasorum (Baillet, 1866) Kamensky", *Parasitol. Res.*, 2007, 102(3):389-395.
Drake, et al., "Molecular and functional characterization of a recombinant protein of Trichuris trichiura", *Proc. Bio. Sci.*, 1998, 265:1559-1565.
Drake, et al., "The major secreted product of the whipworm, *Trichuris*, is a pore-forming protein", *Proc. Bio. Sci*, 1994, 257:255-261.
Gasser, et al., "Improved molecular diagnostic tools for human hookworms", *Expert Rev. Mol. Diagn.*, 2009, 9(1):17-21.
Jenkins et al., "Functional antigens of Trichuris muris released during in vitro maintenance: their immunogenicity and partial purification", *Parasitology*, 1983, 86:73-82.
Johnson, et al., "Detection of gastrointestinal nematodes by a coproantigen capture ELISA", *Res. Vet. Sci.*, 1996, 60:7-12.
Kania et al., "Anoplocephala perfoliata coproantigen detection: a preliminary study", *Vet. Parasitol.*, 2005, 127(2): 115-119.
Lillywhite et al., "Humoral immune responses in human infection with the whipworm *Trichuris trichiura*", Parasite Immunol., 1991, 13:491-507.
Lillywhite et al., "Identification and characterization of excreted/secreted products of Trichuris trichiura", *Parasite Immunol.*, 1995, 17:47-54.
Nukumi et al., "Whey acidic protein (WAP) regulates the proliferation of mammary epithelial cells by preventing serine protease from degrading laminin", *J. Cell. Physiol.*, May 31, 2007, 213:793-800.
Parkinson et al., "400 000 nematode ESTs on the Net", *Trends Parasitol.*, Jul. 2003, 19(7):283-286.
Song et al., "Cross-reactivity between sera from dogs experimentally infected with Dirofilaria immitis and crude extract of Toxocara canis", *Korean J. Parasitol.*, Dec. 2002, 40(4):195-198.
Traub, et al., "Canine gastrointestinal parasitic zoonoses in India", *Trends in Parasit.*, 2005, 21(1):42-48.
Wakelin, "Acquired immunity to Trichuris muris in the albino laboratory mouse", *Parasitology*, 1967, 57:515-524.
GenBank Accession No. AAD01628.1. Jan. 1999. [Retrieved from the Internet Feb. 25, 2010: <URL:http://ncbi.nlm.nih.gov/protein/410955>].
GenBank Accession No. BM965689.1. Mar. 2002. [Retrieved from the Internet Feb. 25, 2010: <URL:http://ncbi.nlm.nih.gov/nucest/19558140>].
GenBank Accession No. BQ088667.1. Apr. 2002. [Retrieved from the Internet Feb. 25, 2010: <URL:http://ncbi.nlm.nih.gov/nucest/20062868>].

(56) References Cited

OTHER PUBLICATIONS

GenBank Accession No. AAC17174.1. May 1998. [Retrieved from the Internet Feb. 25, 2010: <URL:http://ncbi.nlm.nih.gov/protein/3152922>].
GenBank Accession No. AAC47345.1. Oct. 2007. [Retrieved from the Internet Feb. 25, 2010: <URL:http://ncbi.nlm.nih.gov/protein/1663728>].
GenBank Accession No. AAG31482.1. Nov. 2000. [Retrieved from the Internet Feb. 25, 2010: <URL:http://ncbi.nlm.nih.gov/protein/11138792>].
GenBank Accession No. NP_510821. Nov. 2008. [Retrieved from the Internet Feb. 25, 2010: <URL:http://ncbi.nlm.nih.gov/protein/17551598>].
GenBank Accession No. CB098869. Jan. 28, 2003. [Retrieved from the Internet Mar. 30, 2010: <URL:http://ncbi.nlm.nih.gov/nucest/27924676>].
GenBank Accession No. CB099165. Jan. 28, 2003. [Retrieved from the Internet Mar. 30, 2010: <URL:http://ncbi.nlm.nih.gov/nucest/27924972>].
GenBank Accession No. CB099244. Jan. 28, 2003. [Retrieved from the Internet Mar. 30, 2010: <URL:http://ncbi.nlm.nih.gov/nucest/27925051>].
GenBank Accession No. CB099367. Jan. 28, 2003. [Retrieved from the Internet Mar. 30, 2010: <URL:http://ncbi.nlm.nih.gov/nucest/27925174>].
GenBank Accession No. CB188155. Feb. 5, 2003. [Retrieved from the Internet Mar. 30, 2010: <URL:http://ncbi.nlm.nih.gov/nucest/28251547>].
GenBank Accession No. CB188174. Feb. 5, 2003. [Retrieved from the Internet Mar. 30, 2010: <URL:http://ncbi.nlm.nih.gov/nucest/28251566>].
GenBank Accession No. CB188239. Feb. 5, 2003. [Retrieved from the Internet Mar. 30, 2010: <URL:http://ncbi.nlm.nih.gov/nucest/28251631>].
GenBank Accession No. CB188637. Feb. 5, 2003. [Retrieved from the Internet Mar. 30, 2010: <URL:http://ncbi.nlm.nih.gov/nucest/28252029>].
GenBank Accession No. CB189034. Feb. 5, 2003. [Retrieved from the Internet Mar. 30, 2010: <URL:http://ncbi.nlm.nih.gov/nucest/28252426>].
GenBank Accession No. CB189036. Feb. 5, 2003. [Retrieved from the Internet Mar. 30, 2010: <URL:http://ncbi.nlm.nih.gov/nucest/28252428>].
GenBank Accession No. CB189116. Feb. 5, 2003. [Retrieved from the Internet Mar. 30, 2010: <URL:http://ncbi.nlm.nih.gov/nucest/28252508>].
GenBank Accession No. CB189285. Feb. 5, 2003. [Retrieved from the Internet Mar. 30, 2010: <URL:http://ncbi.nlm.nih.gov/nucest/28252677<].
GenBank Accession No. CB189434. Feb. 5, 2003. [Retrieved from the Internet Mar. 30, 2010: <URL:http://ncbi.nlm.nih.gov/nucest/28252826>].
GenBank Accession No. CB277501. Feb. 25, 2003. [Retrieved from the Internet Mar. 30, 2010: <URL:http://ncbi.nlm.nih.gov/nucest/28561086>].
GenBank Accession No. CB277590. Feb. 25, 2003. [Retrieved from the Internet Mar. 30, 2010: <URL:http://ncbi.nlm.nih.gov/nucest/28561175>].
GenBank Accession No. CB277641. Feb. 25, 2003. [Retrieved from the Internet Mar. 30, 2010: <URL:http://ncbi.nlm.nih.gov/nucest/28561226>].
GenBank Accession No. 06277653. Feb. 25, 2003. [Retrieved from the Internet Mar. 30, 2010: <URL:http://ncbi.nlm.nih.gov/nucest/28561226>].
GenBank Accession No. CB277950. Feb. 25, 2003. [Retrieved from the Internet Mar. 30, 2010: <URL:http://ncbi.nlm.nih.gov/nucest/28561535>].
GenBank Accession No. CB188241. Feb. 5, 2003. [Retrieved from the Internet Mar. 30, 2010: <URL:http://ncbi.nlm.nih.gov/nucest/28251633>].
GenBank Accession No. CB277846. Feb. 25, 2003. [Retrieved from the Internet Mar. 30, 2010: <URL:http://ncbi.nlm.nih.gov/nucest/28561431>].
GenBank Accession No. CB277826. Feb. 25, 2003. [Retrieved from the Internet Mar. 30, 2010: <URL:http://ncbi.nlm.nih.gov/nucest/28561411>].
GenBank Accession No. CB189366. Feb. 5, 2003. [Retrieved from the Internet Mar. 30, 2010: <URL:http://ncbi.nlm.nih.gov/nucest/28252758>].
GenBank Accession No. CB098807. Jan. 28, 2003. [Retrieved from the Internet Mar. 30, 2010: <URL:http://ncbi.nlm.nih.gov/nucest/27924614>].
GenBank Accession No. CB189370. Feb. 5, 2003. [Retrieved from the Internet Mar. 30, 2010: <URL:http://ncbi.nlm.nih.gov/nucest/28252762>].
GenBank Accession No. BQ089025. Apr. 5, 2002. [Retrieved from the Internet Mar. 30, 2010: <URL:http://ncbi.nlm.nih.gov/nucest/20063226>].
GenBank Accession No. BM966041. Mar. 20, 2002. [Retrieved from the Internet Mar. 30, 2010: <URL:http://ncbi.nlm.nih.gov/nucest/19558790>].
GenBank Accession No. BQ088880. Apr. 5, 2002. [Retrieved from the Internet Mar. 30, 2010: <URL:http://ncbi.nlm.nih.gov/nucest/20063081>].
Uniprot submission P07852. Aug. 1988. [Retrieved from the Internet Mar. 30, 2010: <URL: http://www.uniprot.org/uniprot/P07852>].
Uniprot submission Q06811. Nov. 1997. [Retrieved from the Internet Feb. 25, 2010: <URL://www.uniprot.org/uniprot/Q06811>].
Uniprot submission Q24702. Nov. 1996. [Retrieved from the Internet Feb. 25, 2010: <URL:http://uniprot.org/uniprot/Q24702>].
Uniprot submission P91811. May 1997. [Retrieved from the Internet Feb. 25, 2010: <URL:http://uniprot.org/uniprot/P91811>].
Uniprot submission O44397. Jun. 1988. [Retrieved from the Internet Nov. 11, 2009: <URL:http://uniprot.org/uniprot/O44397>].
Uniprot submission P19398. Nov. 1, 1990. [Retrieved from the Internet Mar. 30, 2010: <URL: http://www.uniprot.org/uniprot/P19398>].
Uniprot submission O77416. Nov. 1, 1998. [Retrieved from the Internet Mar. 30, 2010: <URL: http://www.uniprot.org/uniprot/O77416>].
Uniprot submission Q2VMT7. Jan. 10, 2006. [Retrieved from the Internet Mar. 30, 2010: <URL: http://www.uniprot.org/uniprot/Q2VMT7>].
Uniprot submission Q9U6V1. May 1, 2000. [Retrieved from the Internet Mar. 30, 2010: <URL: http://www.uniprot.org/uniprot/Q9U6V1>].
Uniprot submission Q16938. Nov. 1, 1996. [Retrieved from the Internet Mar. 30, 2010: <URL: http://www.uniprot.org/uniprot/Q16938>].
Uniprot submission Q962V8. Dec. 1, 2001. [Retrieved from the Internet Mar. 30, 2010: <URL: http://www.uniprot.org/uniprot/Q962V8>].
Ambler, et al., "Biological Techniques for Studying the Allergenic Components of Nematodes. I. Detection of Allergenic Components in *Ascaris suum* Extracts", *J. Immunol. Methods*, vol. 1, No. 4, pp. 317-327, (1972).
Britton, et al., "Extensive diversity in repeat unit sequences of the cDNA encoding the polyprotein antigen/allergen from the bovine lungworm Dictyocaulus viviparous", *Mol. Biochem. Parasitol.* vol. 72, Nos. 1-2, pp. 77-88, (1995).
Christie, et al., "The ABA-1 allergen of the nematode *Ascaris suum*: epitope stability, mass spectrometry, and N-terminal sequence comparison with its homologue in *Toxocara canis*", *Clin. Exp. Immunol.*, vol. 92, pp. 125-132, (1993).
Kennedy, "Stage-specific secreted antigens of the parasitic larval stages of the nematode *Ascaris*" *Immunology*, vol. 58, No. 3, pp. 515-522, (1986).
McGibbon, et al., "Identification of the major Ascaris allergen and its purification to homogeneity by high-performance liquid chromatography", *Mol. Biochem. Parasitol.*, vol. 39, No. 2, pp. 163-171, (1990).

(56) References Cited

OTHER PUBLICATIONS

Meenan, et al., "Resonance assignment of ABA-1A, from *Ascaris suum* nematode polyprotein allergen", *J. Biomol. NMR*, vol. 32, No. 2 p. 176, (2005).

Poole, et al., "Cloning of a cuticular antigen that contains multiple tandem repeats from the filarial parasite *Dirofilaria immitis*", *Proc. Natl. Acad. Sci. USA*, vol. 89, No. 13, pp. 5986-5990, (1992).

Solovyova, et al., "The polyprotein and FAR lipid binding proteins of nematodes: shape and monomer/dimer states in ligand-free and bound forms", *Eur. Biophys. J.*, vol. 32, No. 5, pp. 465-476, (2003).

Spence, et al., "A cDNA encoding repeating units of the ABA-1 allergen of *Ascaris*", *Mol. Biochem. Parasitol*. vol. 57, pp. 339-343, (1993).

The C. elegans consortium, et al., "Genome Sequence of the Nematode *C. elegans*: A Platform for Investigating Biology", *Science*, vol. 282, pp. 2012-2018, (1998).

Tweedie, et al., "Brugia pahangi and Brugia malayi: a surface-associated glycoprotein (gp15/400) is composed of multiple tandemly repeated units and processed from a 400-kDa precursor", *Exp. Parasitol.*, vol. 76, No. 2, pp. 156-164, (1993).

Bethony, J., et al., "Soil-Transmitted Helminth Infections: Ascariasis, Trichuriasis, and Hookworm", Lancet, May 6, 2006, vol. 367, pp. 1521-1532.

Elsemore, D.A., et al., "Enzyme-Linked Immunosorbent Assays for Coproantigen Detection of Ancylostoma caninum and Toxocara canis in Dogs and Toxocara cati in Cats", Journal of Veterinary Diagnostic Investigation, 2017, vol. 29(5), pp. 645-653.

Meltzer, E., "Soil-Transmitted Helminth Infections", Lancet, Jul. 28, 2006, vol. 368, pp. 283-284.

Stave, J.W., et al., "Antibody and Antigen Contact Residues Define Epitope and Paratope Size and Structure", Journal of Immunology, 2013, vol. 191, 8 pages, published online Jun. 24, 2013.

Zhan, B., et al., "Molecular Characterisation of the Ancylostoma-Secreted Protein Family from the Adult Stage of Ancylostoma caninum", International J. Parasitology, 2003, vol. 33, pp. 897-907.

U.S. Appl. No. 16/591,329, filed Oct. 2, 2019.

Babin, et al., "The Isoinhibitors of Chymotrypsin/Elastase from *Ascaris lumbricoides*: The Primary Structure", *Archives of Biochemistry and Biophysics*, vol. 232, No. 1, pp. 143-161, (1984).

Cappello, et al., "*Ancylostoma caninum* anticoagulant peptide: A hookworm-derived inhibitor of human coagulation factor Xa", *Proc. Natl. Acad. Sci.*, vol. 92, pp. 6152-1656, (1995).

Ford, et al., "Characterization of a Novel Filarial Serine Protease Inhibitor, Ov-SPI-1, from *Onchocerca volvulus*, with Potential Multifunctional Roles during Development of the Parasite", *J. of Biol. Chem.*, vol. 280, No. 49, pp. 40845-40856, (2005).

Fraefel, et al., "The amino acid sequence of a trypsin inhibitor isolated from ascaris (*Ascaris lumbricoides* var. *suum*)", *Biochim. Biophys. Acta*, vol. 154, pp. 615-617, (1968).

Goodman, et al., "Isolation of the Trypsin Inhibitors in *Ascaris lumbricoides* var. *suum* Using Affinity Chromatography", *Analytical Biochemistry*, vol. 120, pp. 387-393 (1982).

Grasberger, et al., "High-resolution structure of *Ascaris* trypsin inhibitor in solution: direct evidence for a pH-induced conformational transition in the reactive site", *Structure*, vol. 2, No. 7, pp. 669-678, (1994).

Gronenborn, et al., "Sequential resonance assignment and secondary structure determination of the Ascaris trypsin inhibitor, a member of a novel class of proteinase inhibitors", *Biochemistry*, vol. 29, No. 1, pp. 183-189, (1990).

Harrison, et al., "Molecular Characterization of *Ancylostoma* Inhibitors of Coagulation Factor Xa", *J. of Biol. Chem.*, vol. 277, No. 8, pp. 6223-6229, (2002).

Hawley, et al., "*Ascaris suum*: Are Trypsin Inhibitors Involved in Species Specificity of Ascarid Nematodes?", *Experimental Parasitology*, vol. 75, pp. 112-118 (1992).

Huang, et al., "The molecular structure of the complex of Ascaris chymotrypsin/elastase inhibitor with porcine elastase", *Structure*, vol. 2, No. 7, pp. 679-689, (1994).

Lu, et al., "*Anisakis simplex*: Mutational Bursts in the Reactive Site Centers of Serine Protease Inhibitors from an Ascarid Nematode", *Experimental Parasitology*, vol. 89, pp. 257-261, (1998).

Martzen, et al., "*Ascaris suum*: Localization by Immunochemical and Fluorescent Probes of Host Proteases and Parasite Proteinase Inhibitors in Cross-sections", *Experimental Parasitology*, vol. 60, pp. 139-149, (1985).

Nguyen, et al., "Expression and characterization of elastase inhibitors from the ascarid nematodes *Anisakis simplex* and *Ascaris suum*", *Mol. Biochem. Parasitology*, vol. 102, pp. 79-89, (1999).

Peanasky, et al., "The Isoinhibitors of Chymotrypsin/Elastase from *Ascaris lumbricoides*: Isolation by Affinity Chromatography and Association with the Enzymes", *Archives of Biochemistry and Biophysics*, vol. 232, No. 1, pp. 127-134, (1984).

Rhoads, et al., "*Trichuris suis*: A Secretory Serine Protease Inhibitor", *Experimental Parasitology*, vol. 94, pp. 1-7, (2000).

Rhoads, et al., "*Trichuris suis*: A Secretory Chymotrypsin/Elastase Inhibitor with Potential as an Immunomodulator", *Experimental Parasitology*, vol. 95, pp. 36-44, (2000).

Stanssens, et al., "Anticoagulant repertoire of the hookworm *Ancylostoma canium*", *Proc. Natl. Acad. Sci.*, vol. 93, pp. 2149-2154, (1996).

Uniprot submission P07851. Aug. 1988. [Retrieved from the internet Dec. 13, 2009:, URL:http://www.uniprot.org/uniprot/P07851.] in entirety.

Bailey, "The Raising of a Polyclonal Antiserum to a Protein", *Methods Mol. Biol.*, vol. 32, pp. 381-388, (1994).

Barker, et al., "Isolation of a gene family that encodes the porin-like proteins from the human parasitic nematode *Trichuris trichiura*", *Gene*, vol. 229, pp. 131-136, (1999).

Dean, "Preparation and Characterization of Monoclonal Antibodies to Proteins and Other Cellular Components", *Methods Mol. Biol.*, vol. 32, pp. 361-379, (1994).

Dean, "Preparation and Testing of Monoclonal Antibodies to Recombinant Proteins", *Methods Mol. Biol.*, vol. 80, pp. 23-37, (1998).

Drenckhahn, et al., "Production of Polyclonal Antibodies against Proteins and Peptides", *Methods Cell Biol.*, vol. 37, pp. 7-56, (1993).

Dryden, et al., "Comparison of Common Fecal Flotation Techniques for the Recovery of Parasite Eggs and Oocysts", *Vet. Ther.*, vol. 6, No. 1, pp. 15-28, (2005).

Gullick, "Production of Antisera to Synthetic Peptides", *Methods Mol. Biol.*, vol. 32, pp. 389-399, (1994).

Kennedy, "The Nematode Polyprotein Allergens/Antigens", *Parasitol. Today*, vol. 16, No. 9, pp. 373-380, (2000).

Memoranda, "Parasite Antigens", *Bull. World Health Organ*, vol. 52, pp. 237-249, (1975).

Morrison, "In Vitro Antibodies: Strategies for Production and Application", *Annu. Rev. Immunol.*, vol. 10, pp. 239-265, (1992).

Prociv et al., "Human enteric infection with *Ancyostoma caninum*: hookworms reappraised in the light of a "new" zoonosis", *Acta. Tropica.*, vol. 62, pp. 23-44, (1996).

Wright, et al., "Genetically Engineered Antibodies: Progress and Prospects", *Crit. Rev. Immunol.*, vol. 12 (3-4), pp. 125-168, (1992).

Xia, et al., "The ABA-1 allergen of Ascaris lumbricoides: sequence polymorphism stage and tissue-specific expression, lipid binding function and protein biophysical properties", *Parasitology*, vol. 120 (Pt.2), pp. 211-224, (2000).

Yahiro, et al., "Identification, characterization and expression of Toxocara canis nematode polyprotein allergen TBA-1", *Parasite Immunol.*, vol. 20, No. 8, pp. 351-357, (1998).

Abdel-Rahman et al., Evaluation of a diagnostic monoclonal antibody-based capture enzyme-linked immunosorbent assay for detection of a 26- to 28-kd Fasciola hepatica coproantigen in cattle, *American Journal of Veterinary Research* 59:533-537 (1998).

Bungiro and Cappello, "Detection of Excretory/Secretory Coproantigens in Hookworm infection," *Am. J. Trop. Med. Hyg.* 73(5):915-920 (2005).

Bungiro, Jr., et al., "Purification and Molecular Cloning of and Immunization with Ancylostoma ceylancium Excretory-Secretory Protein 2, an Immunocreactive Immunoreactive Protein Produced by Adult Hookworms," *Infection and Immunity* 72(4):2203-2213 (2004).

(56) References Cited

OTHER PUBLICATIONS

Carleton et al., Prevalence of Dirofilaria immitis and gastrointestinal helminths in cats euthanized at animal control agencies in northwest Georgia, *Veterinary Parisitology* 119:319-326 (2004).

Coulaud, J.P., et al., Albendazole: a new single dose anthelmintic. Study in 1455 patients, *Acta Tropica* 41:87-90 (1984).

De Oliveira et al., IgM-ELISA for diagnosis of schistosomiasis mansoni in low endemic areas, Cadernos de saude publica / Ministêrio da Saude, Fundacao Oswaldo Cruz, Escola Nacional de Saude Publica 19:255-261 (2003).

Deplazes et al., Detection of Taenia hydatigena copro-antigens by ELISA in dogs, *Veterinary Parisitology* 36:91-103 (1990).

Dumenigo et al., Kinetics of antibody-based antigen detection in serum and faeces of sheep experimentally infected with Fasciola hepatica, *Veterinary Parisitology* 86:23-31 (1999).

Foreyt, W.J., Veterinary Parasitology Reference Manual, Fifth Edition, 2001, ISBN 0-8138-2419-2, pp. 3-10.

Hill et al., "ATrichuris specific diagnostic antigen from culture fluids of Trichuris suis adult worms", *Veterinary Parasitology*, vol. 68, pp. 91-102, (1997).

IDEXX Laboratories Canine Paravovirus Antigen Test Kit package insert (English Section Only).

Martinez-Maya et al., Taeniosis and detection of antibodies against Cysticeri among inhabitants of a rural community in Guerro State, Mexico, Salud Publica de Mexico 45:84-89 (2003).

Ott et al., Demonstration of both immunologically unique and common antigenic determinants in Dirofilaria immitis and Toxocara canis using monoclonal antibodies, *Veterinary Immunology and Immunopathology* 10:147-153 (1985).

Roberts, L.S., et al., Foundations of Parasitology, Fifth Edition, 1996, Library of Congress Card Catalog No. 94-72939, ISBN 0-687-26071-S, pp. 1-4.

Southworth, Exine development in *Gerbera jamesonii* (Asteraceae: Mutisieae), *American Journal of Botany*, 70:1038-1047 (1983).

Voller, "The Enzyme Linked Immunosorbent Assay", *Diagnostic Horizon*, vol. 2, No. 1, pp. 1-7, Feb. 1978.

Willard et al., Diagnosis of Aelurostrongylus abstrusus and Dirofilaria immitis infections in cats from a human shelter, *Journal of the American Veterinary Medical Association* 192:913-916 (1988).

Yamasaki et al., "Development of Highly Specific Recombinant Toxocara canis Second-Stage Larva Excretory-Secretory Antigen for Immunodiagnosis of Human Toxocariasis," Journal of Clinical Microbiology 38 (4):1409-1413 (2000).

Zhan et at, "Molecular characterisation of the Ancylostoma-secreted protein family from the adult stage of Ancylostoma caninum," *International Journal for Parasitology* 33:897-907 (2003).

Westermarck, et al., "Faecal hydrolase activity as determined by radial enzyme diffusion: a new method for detecting pancreatic dysfunction in the dog", *Res. Vet. Sci.*, vol. 28, No. 3, pp. 341-346, (1980) (Abstract).

Williams, et al., "Comparison of methods for assay of the fecal proteolytic activity", *Vet. Clin. Pathol.*, vol. 19, No. 1, pp. 20-24, (1990) (Abstract).

Williams, et al., "Fecal proteolytic activity in clinically normal cats and in a cat with exocrine pancreatic insufficiency", *J. Am. Vet. Med. Assoc.*, vol. 197, No. 2, pp. 1112-1113, 1116, (1990) (Abstract).

Uniprot Submission P91811. May 1997 [Retrieved from the internet Nov. 7, 2009: [URL:http://www.uniprot.org/uniprot/P91811].

Uniport submission O44397. Jun. 1988 [Retrieved from the internet Nov. 11, 2009: [<URL:http://www.uniport.org/uniport/O44397>].

NCBI Blast: SEQ ID No. 4 (Performed Aug. 27, 2009 using http://blast.ncbi.nlm.nih.gov/blast.cgi).

Altschul, et al., "Gapped BLAST and PSI-BLAST: a new generation of protein database search programs", *Nucl. Acids. Res.*, vol. 25, No. 17, pp. 3389-3402, (1997).

Karlin, et al. "Applications and statistics for multiple high-scoring segments in molecular sequences," *Prov. Natl. Acad. Sci. USA*, vol. 90, pp. 5873-5877, (1993).

Karlin, et al. "Methods for assessing the statistical significance of molecular sequence features by using general scoring schemes", *Proc. Natl. Acad. Sci. USA*, vol. 87, pp. 2264-2268, (1990).

\* cited by examiner

FIG. 1

MPNLLLLFLSLPGAILSTTCPGNDLTDAERTLLTRVHNSIRREIAQGVANNYHGGKLPAGKNIY
RMRYSCELEQAAIDASQTFCSASLEEPQKYGQNIQAYVTPSIIARPKNDLLEDAVKQWYLPVIYY
GQRDAANKFTDPRLYTFANLAYDKNTALGCHYAKCQGPDRIVISCMYNNVPDNAVIYEPGTACV
KDADCTTYPQSTCKDSLCIIPTPHPPNPPPAMSPN**AEMTDAARKKVLGMHNWRRSQVALGNV
QNGKNAYNCPTATDMYKIEYDCDLENSALAYAK**QCSLVGSAEGTRPGEGENVHKGALVTDPEAAV
QTAVQAWWSQISQNGLNAQMKFTAFLKDKPDAPTAFTQMAWAKSVKLGCAVSNCQADTFTVCRYK
AAGNIVGEFIYTKGNVCDACKATCITAEGLCPTP    [SEQ ID NO:5]

Notes: 1. KQ is in both peptide 1 (C-terminus) and 2 (N-terminus)
       2. KN is in both peptide 3 (N-terminus) and 4 (C-terminus)
       3. Asp5-2 is blue
       4. MS peptides:
          1. K.NDLLEDAVK.Q          [SEQ ID NO:6]
          2. K.QWYLPVIYYGQR.D       [SEQ ID NO:7]
          3. R.LYTFANLAYDK.N        [SEQ ID NO:8]
          4. K.NTALGCHYAK.C         [SEQ ID NO:9]

COMPOSITIONS, DEVICES, KITS AND METHODS FOR DETECTING HOOKWORM

CROSS REFERENCE

This application is a divisional of U.S. patent application Ser. No. 14/974,659, filed Dec. 18, 2015 (now U.S. Pat. No. 10,640,551), which is a divisional of U.S. patent application Ser. No. 12/467,778, filed May 18, 2009 (now U.S. Pat. No. 9,239,326), which claims the benefit of priority to U.S. Provisional Patent Application Ser. No. 61/122,254, filed Dec. 12, 2008, and is a continuation-in-part of U.S. application Ser. No. 11/763,583, filed Jun. 15, 2007 (now U.S. Pat. No. 9,063,129), all which are incorporated by reference herein in its entirety.

BACKGROUND OF THE INVENTION

Field of the Invention

The present invention relates to compositions, devices, kits and methods for the detection of hookworm in mammals. More particularly, the present invention relates to polypeptides and polypeptide compositions, antibodies and antibody compositions, devices, kits, and methods for detecting the presence or absence of hookworm antigen in a sample from a mammal that may also include one or more of roundworm, whipworm, and heartworm antigen.

Description of the Prior Art

Hookworms are bloodsucking intestinal parasites that can cause their host to suffer serious illness, such as anemia, wasting and retarded development. For example, the hookworm *Ancylostoma caninum* causes significant disease in both dogs and humans (Prociv et al., Acta Trop. 1996 Sep.; 62(1):23-44).

Current methods for diagnosis of hookworm infections primarily involve microscopic examination of fecal samples, either directly in fecal smears or following concentration of ova by flotation in density media. Despite this procedure's high adoption, the method has significant shortcomings. These microscopic methods are time consuming, are unpleasant, require specialized equipment and can have low specificity [Dryden et al., 2005. Vet Therap. 6(1), 15-28]. In addition, the accuracy of results of these methods is highly dependent upon the skill and expertise of the operator. (For example, a novice eye often will mistake ova of other parasitic nematodes for those of hookworm and vice versa.) This potential for misdiagnosis is unfortunate because a misdiagnosed animal may be given a treatment that is ineffective against hookworm, and therefore one that would not alleviate the animal's suffering or stop the progressive wasting of its health.

Stool handling is disagreeable and hazardous. Sanitary and inoffensive procedures for processing stool are awkward and often complex. Such procedures may include weighing, centrifuging and storing, and are difficult except in a clinical laboratory equipped with a suitable apparatus, protective equipment, and a skilled technician. Therefore, any reduction in the number of steps required to perform a fecal test and any reduction in contact between test operator and the test material is desirable. Clinical laboratories have been using the immunoassay methods for the detection of various viruses, bacteria and non-helminth parasites and organisms in feces. However, there remains a need for a simple immunoassay method for the detection of a parasitic worm infection, and hookworm infection in particular in feces, whole blood or in serum.

Another significant limitation of diagnosis by microscopic detection of ova is that because hookworm eggs generally are not detectable in host feces until well after infection manifests, it does not allow for early detection of hookworm infection. For example, hookworm ova generally do not appear in canine feces until about 17 days after oral ingestion of the parasite by the canine. This is a problem because symptoms such as severe weight loss and bloody diarrhea often distress the host before hookworm ova first appear in the feces. Early detection therefore is highly desirable.

SUMMARY OF THE INVENTION

In one aspect, the invention includes antibodies that specifically bind to a polypeptide including all or an antigenic portion of the amino acid sequence that corresponds to SEQ ID NOS:1 AND 2, as listed herein, or to a polypeptide including a sequence that is a conservative variant of one of those sequences. In a further aspect, the antibodies specifically bind to antigen from hookworm infested mammals, but do not specifically bind antigen from mammals infected with roundworm, whipworm and/or heartworm.

In another aspect, the invention includes antibodies that are obtained by immunization with the polypeptide including all or an antigenic portion of the amino acid sequence that corresponds to SEQ ID NOS:1 AND 2, or with a polypeptide including a sequence that is a conservative variant of one of those sequences.

In yet another aspect, the invention provides a device for detecting the presence or absence of hookworm in a sample from a mammal, comprising a solid support, wherein one or more of the antibodies of the invention are immobilized on the solid support. The device may be, but is not limited to being, for example, an ELBA device, such as a lateral flow immunoassay device or microtiterplate device. Mammalian samples that may be tested for hookworm by the device include, but are not limited to being, feces, whole blood, serum, mammary milk and whole tissue, such as tissue from the respiratory system, mammary gland, mucosa, intestine, liver, heart, lung, esophagus, brain, muscle, and eye, for example. The device further may include, but need not include, one or more reagents for the detection of one or more of the group consisting of: one or more non-hookworm worm parasites, one or more non-worm parasites, one or more viruses, one or more fungi, and one or more bacteria.

In yet another aspect, the invention provides a method of detecting the presence or absence of hookworm, such as *Ancylostoma caninum, Ancylostoma braziliense, Ancylostoma duodenal, Ancylostoma ceylanicum, Ancylostoma tubaeforme* and *Ancylostoma pluridentatum Necator americanus*, and *Uncinaria stenocephala*, for example, in a sample obtained from a mammal, such as a canine, feline, porcine, bovine, or human. In one aspect, the method is carried out to test a fecal sample for hookworm coproantigen. The method, however, is not limited to being carried out to test a fecal sample. In addition to feces, the sample therefore may be, but is not limited to being whole blood, serum, mammary milk and whole tissue, such as tissue from the respiratory system, mummy gland, mucosa, intestine, liver, heart, king, esophagus, brain, muscle, and eye, for example. Steps of the method include contacting the sample with one or more of the antibodies of the invention and detecting the presence or absence of one or more hookworm antigens, such as the polypeptides of the invention, for example, or detecting the presence or absence of one or more complexes that include one or more hookworm antigens and one or more antibodies of the invention. The method further may include one or more of the optional steps of diagnosing the mammal as either having or not having a hookworm infection and determining whether a nucleic acid from hookworm is present in the same sample that was contacted with the antibodies for the purpose of detecting the presence or absence of hookworm or in some other sample from the mammal. The method may also be used to test for environmental contamination with hookworm. Environmental samples that may be tested for hookworm by the device include, but are not limited to soil, decomposing material, or fecal matter from residential settings including yards, gardens, sand boxes, and playgrounds. Testing locations may also include parks, beaches, forests, farms, or other locations exposed to fecal material from dogs, cats, or other mammalian hosts of hookworms. Feces from indoor and outdoor litter boxes may also be tested.

In yet another aspect, the present invention includes a kit for canning out one or more steps of the method of the invention. The kit may optionally include, for example, the device and one or more of the compositions of the present invention and instructions for carrying out the method of the present invention. The kit may further optionally include, for example, one or more indicator reagents, one or more antibody labeling compounds, one or more antibodies, one or more antigen capture reagents, one or more inhibitors, and one or more wash reagents to be used as part of the device and/or to be used in carrying out the method.

BRIEF DESCRIPTION OF THE DRAWINGS

FIG. 1 shows mass spectroscopy data identifying the 28 kDa fragment as an N-terminal fragment of ASP5 (SEQ ID NO:5). MS Peptides 1-4 are SEQ ID Nos:6-9, respectively.

DETAILED DESCRIPTION OF THE PREFERRED EMBODIMENTS OF THE INVENTION

I. Introduction

Figure 2:
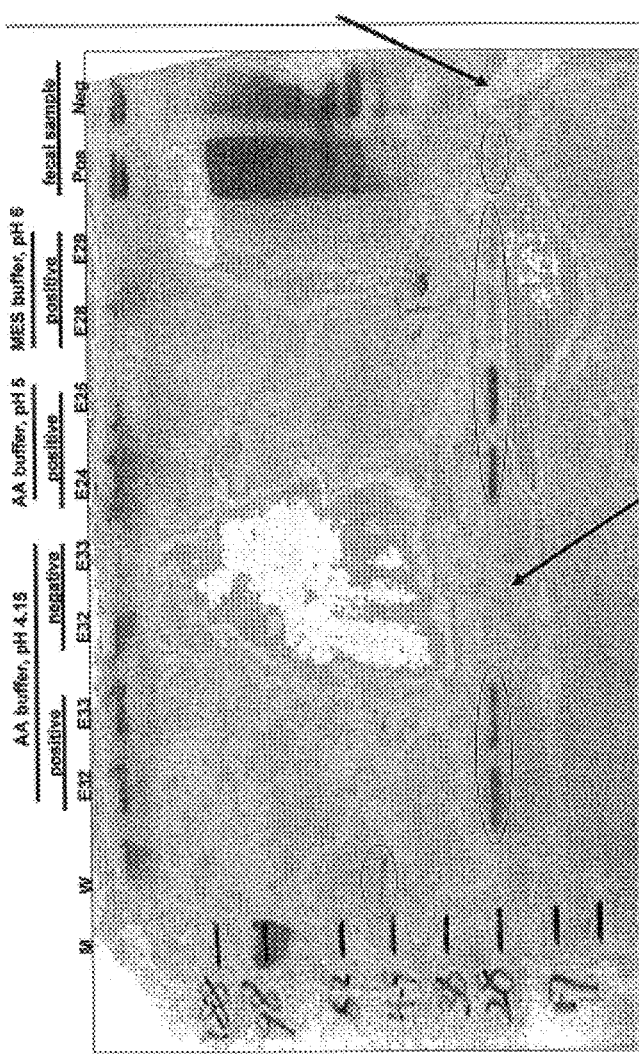
FIG. 2 shows a Western blot showing the binding of anti-Ac-ASP-5 pAB to a product of about 56 kDa in extract of whole hookworm.

The present invention is generally directed to methods, devices, kits and compositions for detecting hookworm in a sample, which may be, for example, a fecal sample obtained from a mammal or anything that has contacted a mammalian fecal sample, such as soil, sand, grass, leaves, decomposing material, etc. The present invention relates to hookworm antigens from *Ancylostoma*, such as *Ancylostoma caninum, Ancylostoma braziliense, Ancylostoma duodenal, Ancylostoma ceylanicum, Ancylostoma tubaeforme* and *Ancylostoma pluridentatum*, for example. The present invention also relates to hookworm antigens from *Necator*, such as *Necator americanus*, for example, and from *Uncinaria* such as *Uncinaria stenocephala* for example. In particular, the present invention relates to polypeptides and conservative variants thereof, polynucleotides that encode those polypeptides and oligonucleotides that specifically bind to those polynucleotides, antibodies that are raised against and that specifically bind those polypeptides, and methods, devices, compositions and kits for detecting hookworm, such as *Ancylostoma, Necator* and *Uncinaria*, for example.

The present invention is based in part on the discovery of unexpected properties of compositions of the present invention. Specifically, it was determined that an antibody of the present invention raised against a polypeptide of the present invention can be used to capture and detect hookworm antigens in a mammal, even when the mammal is also infested by one or more of roundworm, whipworm and heartworm. This specificity for hookworm is surprising because hookworms, whipworms, roundworms and heartworms all are related nematodes, and an antibody raised against a protein isolated from any one of these worms would be expected to crossreact with one or more of the other worms, host antigens, or other host components.

It was further determined that this antibody can be used to capture and detect hookworm in a mammal as early as 9 days after the mammal is first infected with hookworm. This ability to detect hookworm so soon after infection is surprising because hookworm ova generally do not appear in the feces of an infective host until about 17 days after the host becomes infected.

The present invention therefore includes methods, devices, compositions and kits that use antibodies and/or fragments thereof to specifically capture and detect hookworm in a mammal that may also be infested by one or more of whipworm, hookworm and heartworm. The ability of the present invention to detect and diagnose hookworm even when one or more other worm types are also present allows the mammal's caregiver the opportunity to optimally select a treatment for ridding the hookworm from the mammal. Furthermore, the ability of the present invention to, in some cases, detect hookworm as early as 9 days after the mammal is first infected provides the possibility that the caregiver may begin such treatment before the mammal becomes severely sickened by the hookworm. An intervention prior to appearance of ova in the feces would also greatly reduce or eliminate the possibility that the infestation is spread to other animals or humans.

II. Definitions and Uses of Terms

The term "compositions of the invention" refers to all of the nucleic acids, polypeptides, antibodies, and mixtures that include one or more of those nucleic acids, polypeptides, and antibodies and one or more other compounds, that can be used to detect the presence or absence of hookworm in a sample obtained from a mammal by carrying out the method of the present invention that are explicitly described, implicitly encompassed or otherwise disclosed herein.

"A sample from a mammal" in which hookworm can be detected by the present invention includes all bodily components and extracts thereof, such as any fluid, solid, cell or tissue, that are capable of containing hookworm antigen. Exemplary samples therefore include, but are not limited to being, feces, milk, whole blood and portions thereof, including serum, and further include tissue extracts, including tissue from the respiratory system, mammary gland, mucosa, intestine, liver, heart, esophagus, brain, muscle, and, eye, for example. The sample may be taken directly from the mammal or the sample may be taken from anything that has contacted the mammal or, conversely, any part of the mammal that has contacted the sample. For example, the sample may be fresh or decaying fecal droppings from the mammal. As another example, the sample may include soil, dirt, sand, plant material, or any other material that may be mixed with bodily components that may be left behind by a mammal, such as feces, for example. As another example, the sample may be the mucus at the terminal end of the digestive tract which has come into contact with the mammal's feces. Regardless of the origin or the content of the sample, this sample sometimes is referred to herein as the "mammalian sample", the "test sample" or the "sample, under test".

As used herein, "nucleic acid" is synonymous with, and therefore is used interchangeably with, "gene", "DNA", "cDNA", "EST", "polynucleotide", "oligonucleotide", "polynucleic acid", "RNA" and "mRNA". A nucleic acid may be in double-stranded form or it may be in single-stranded form. Furthermore, a nucleic acid is either naturally isolated, such as from a whole hookworm or a portion thereof, for example, or it is artificially synthesized, either in a recombinant host organism or by any other artificial means known to the skilled artisan, such as by employing a PCR-based technique, by creating a transgenic organism that synthesizes the nucleic acid, by using a DNA synthesizing machine, or by any another molecular-based technique, for example.

"Polypeptide", "peptide" and "protein" are synonymous terms that are used interchangeably herein to refer to a polymer of amino acid residues. A polypeptide, peptide and protein of the present invention may be either naturally isolated, such as from a whole hookworm or from a portion of hookworm, for example, or artificially synthesized, either in a recombinant host organism or by any other artificial means known to the skilled artisan.

The term "antibody" or "antibody of the present invention" refers to any antibody that is able to specifically bind to one or more hookworm antigens, but not to any antigen from roundworm, whipworm or heartworm. The antibodies of the present invention may be raised against one or more immunogenic polypeptides of the present invention. Unless otherwise stated, it is to be understood that the antibody of the present invention may include a mixture of two or more different types of antibody. For example, the antibody may be a mixture of two types of antibodies, wherein one of the two types specifically binds to one particular antigen and the other of the two types specifically binds to some other antigen.

The "immunogenic polypeptide of the present invention" and, more simply, "the polypeptide of the present invention", is an immunogen against which the antibodies of the present invention may be raised. All "polypeptides of the present invention" are immunogenic and therefore may be used to elicit an immune response in a host animal to produce the antibodies of the present invention. Unless otherwise stated, it is to be understood that the polypeptide of the present invention may be one component of a mixed composition of a plurality of components.

An "immunogen" is any agent, such as the immunogenic polypeptide of the present invention, for example, that is capable of eliciting an immune response in an animal that is exposed to that agent.

The term "hookworm", as used herein, refers to helminths such as intestinal hookworms of the order Strongiloidae and family Ancylostomatidae, which includes the genera *Ancylostoma, Uncinaria*, and *Necator*. Thus, the term "hookworm", as used herein, does not refer to the entirety of the phylum Nematoda. For example, "hookworm" does not include any member of the genera *Trichuris, Dirofilaria, Toxocara, Toxascaris, Baylisascaris, Ascaridia, Porascaris*, or *Ascaris*.

A "hookworm coproantigen" or a "coproantigen of hookworm" is any hookworm product that is present in the feces of a mammal having a hookworm infection and that may be specifically bound by one or more of the antibodies of the invention. For example, a hookworm coproantigen may be, but is not limited to being, one or more of the polypeptides of the invention. The present inventors have determined that a novel N-terminal 28 kDa isoform of ASP5, which is a excretory secretory protein of *Ancylostoma*, is present in feces of *Ancylostoma*-infected canines as early as 9 days after the canines first became infected with the *Ancylostoma*. Therefore, a "hookworm coproantigen" may be this novel N-terminal 28 kDa isoform of ASP5 (which is referred to herein as "CoproASP5") that has been observed in canine feces by the present inventors.

"Specific for", "specifically binds", and "stably binds" means that a particular composition of the invention, such as an antibody, polypeptide, or oligonucleotide of the present invention, for example, recognizes and binds to one or more other agents with greater affinity than to at least one other agent. As one example, an antibody of the present invention is said to be "specific for", to "specifically bind", and to "stably bind" hookworm antigens whenever that antibody is able to recognize and bind to those hookworm antigens with greater affinity than to any other antigens from a non-hookworm parasitic worm. Such binding specificity can be tested using methodology well known in the art, for example, ELISA or a radioimmunoassay (RIA). Based on information observed regarding the binding specificity of a particular composition of the invention, the method of the present invention can be carried out under conditions that allow that composition to bind to (and therefore to allow the detection of such binding to) a particular agent or agents, but not to significantly bind other agents, while those conditions are maintained. As one example, the method of the present invention can be carried out under conditions that allow an antibody of the present invention to bind to (and therefore to allow the detection of such binding to) one or more bookworm antigens present in a particular sample, but not significantly to any roundworm, whipworm or heartworm antigen that may be present in that sample.

"Detecting hookworm" means detecting one or more hookworm-specific product, including one or more of the polypeptides, antibodies and nucleic acids of the present invention, one or more hookworm antigens, or CoproASP5, for example. The presence of one or more such hookworm products in a sample from a mammal is indicative that the mammal has a hookworm infection, regardless of whether any whole hookworm organism, ovum or other portion thereof is also present in that sample. Conversely, the absence of one or more such hookworm products a sample from a mammal is indicative that the mammal does not have a hookworm infection.

"Amino acid" refers to naturally occurring and synthetic amino acids. Amino acid residues are abbreviated as follows: Alanine is A or Ala; Arginine is R or Arg; Asparagine is N or Asn; Aspartic Acid is D or Asp; Cysteine is C or Cys; Glutamic Acid is E or Glu; Glutamine is Q or Gln; Glycine is G or Gly; Histidine is H or His; Isoleucine is I or Ile: Leucine is L or Leu; Lysine is K or Lys; Methionine is M or Met; Phenylalanine is F or Phe; Proline is P or Pro; Serine is S or Ser: Threonine is T or Thr; Tryptophan is W or Trp;

Tyrosine is Y or Tyr; and Valine is V or Val. Except where defined otherwise herein, X or Xaa represents any amino acid. Other relevant amino acids include, but are not limited to being, 4-hydroxyproline and 5-hydroxylysine. In all cases, the amino acid sequence of a polypeptide described or otherwise referred to herein is presented in conventional form in that the left-most, or first, amino acid residue of the sequence is the N-terminal residue and the right-most, or last, amino acid residue of the sequence is the C-terminal residue.

A "conservative variant" of any particular nucleic acid sequence includes any sequence having one or more degenerate codon substitutions to that particular nucleic acid sequence, any sequence having one or more nucleotide substitutions to, insertions to, and deletions from that particular nucleic acid sequence, and the complementary sequence of that particular nucleic acid and the conservative variants of that complementary sequence. Conservative variants of a particular nucleic acid sequence preferably have at least about 85% identity, more preferably have at least about 90% identity, and even more preferably at least about 95-99% identity, to that particular nucleic acid sequence. Conservative variants of a particular nucleic acid sequence may be artificially synthesized or they may be isolated in their natural form from an organism, including from a hookworm organism, such as *Ancylostoma caninum*, for example.

A "conservative variant" of any particular polypeptide sequence is any polypeptide having an amino acid sequence that varies from the amino acid sequence of that particular polypeptide but still retains the specific binding properties of that particular polypeptide, such that an antibody of the present invention that is raised against the particular polypeptide is capable of specifically binding the variant polypeptide. Therefore, for example, a conservative variant of a particular polypeptide may have one or more amino acid substitutions, deletions, additions, and insertions to that particular polypeptide. For example, a conserved variant of a particular polypeptide may have 30 or fewer, 25 or fewer, 20 or fewer, 15 or fewer, 10 or fewer, or 5 or fewer, conserved amino acid substitutions to that particular polypeptide. Conservative variants of a particular polypeptide preferably, but not essentially, have at least about 80% identity, more preferably have at least about 90% identity, and even more preferably at least about 91-99% identity, to that particular polypeptide. A percent identity for any subject nucleic acid or amino acid sequence (e.g., any of polypeptides described herein) relative to another "target" nucleic acid or amino acid sequence can be determined as follows. First, a target nucleic acid or amino acid sequence of the invention can be compared and aligned to a subject nucleic acid or amino acid sequence, using the BLAST 2 Sequences (Bl2seq) program from the stand-alone version of BLASTZ containing BLASTN and BLASTP (e.g., version 2.0.14). Instructions explaining how to use BLASTZ, and specifically the Bl2seq program, can be found in the 'readme' file accompanying BLASTZ. The programs also are described in detail by Karlin et al. (1990) *Proc. Natl. Acad. Sci.* 87:2264; Karlin et al. (1990) Proc. Natl. Acad. Sci. 90:5873; and Altschul et al. (1997) *Nucl. Acids Res.* 25:3389.

"CoproASP5" refers to an N-terminal 28 kD fragment of ASP5 found in mammalian feces.

Bl2seq performs a comparison between the subject sequence and a target sequence using either the BLASTN (used to compare nucleic acid sequences) or BLASTP (used to compare amino acid sequences) algorithm. Typically, the default parameters of a BLOSUM62 scoring matrix, gap existence cost of 11 and extension cost of 1, a word size of 3, an expect value of 10, a per residue cost of 1 and a lambda ratio of 0.85 are used when performing amino acid sequence alignments. The output file contains aligned regions, of homology between the target sequence and the subject sequence. Once aligned, a length is determined by counting the number of consecutive nucleotides or amino acid residues (i.e., excluding gaps) from the target sequence that align with sequence from the subject sequence starting with any matched position and ending with any other matched position. A matched position is any position where an identical nucleotide or amino acid residue is present in both the target and subject sequence. Gaps of one or more residues can be inserted into a target or subject sequence to maximize sequence alignments between structurally conserved domains (e. g., α-helices, β-sheets, and loops).

The percent identity over a particular length is determined by counting the number of matched positions over that particular length, dividing that number by the length and multiplying t re resulting value by 100. For example, if (i) a 500 amino acid target sequence is compared to a subject amino acid sequence, (ii) the Bl2seq program presents 200 amino acids from the target sequence aligned with a region of the subject sequence where the first and last amino acids of that 200 amino acid region are matches, and (iii) the number of matches over those 200 aligned amino acids is 180, then the 500 amino acid target sequence contains a length of 200 and a sequence identity over that length of 90% (i.e., 180/200×100=90). It will be appreciated that a nucleic acid or amino acid target sequence that aligns with a subject sequence can result in many different lengths with each length having its own percent identity. It is noted that the percent identity value can be rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

Conservative variants of a particular polypeptide sequence may be artificially synthesized or they may be isolated in their natural form from an organism, including from a hookworm organism, such as *Ancylostoma caninum*, for example. The skilled artisan will recognize that these conserved variants include, but are not limited to, those sequences having one or more substitutions of basic amino acid residues, one or more substitutions of acidic amino acid residues, one or more substitutions of polar amino acid residues, one or more substitutions of hydrophobic amino acid residues, one or more substitutions of aromatic amino acid residues, and one or more substitutions of small amino acid residues, ("Basic" amino acid residues are K, R and H. "Acidic" amino acid residues are D and E. "Polar" amino acid residues are N and Q. "Hydrophobic" amino acids are I, L, and V. "Aromatic" amino acid residues are F, Y, and W. "Small" amino acids are G, S, A, T and M.)

I. Nucleic Acids and Polypeptides of the Invention

The nucleic acids and polypeptides of the invention are described in detail in Provisional Application: "Methods, Devices, Kits And Compositions For Detecting Hookworm" U.S. application Ser. No. 61/122,254, filed Dec. 12, 2008, and is incorporated by reference in its entirety.

Previously, Zhan and colleagues described the molecular identification and partial characterization of ASP-5, which is an excretory/secretory protein of *Ancylostoma* (See Zhan et al., *International Journal for Parasitology* 33:897-907 (2003)). In their studies, the Zhan group described a single form of the ASP-5 protein having a mass of about 56 kDa, secreted from in vitro cultured parasites. The ASP-S protein including an N-terminal His6 tag (SEQ ID NO:2) may be encoded by the nucleic sequence of SED ID NO:1:

(SEQ ID NO: 1)
ATGGGCAGCAGCCATCATCATCATCATCACAGCAGCGGCCTGGTGCCGCG

CGGCAGCCATATGGCTAGCATGACTGGTGGACAGCAAATGGGTCGCGGAT

CCGAATTCGAGCTCACCACTTGTCCAGGAAATGATCTAACAGATGCTGAA

CGCACACTGCTAACTAGGGTGCACAATTCCATTCGACGGGAAATAGCGCA

AGGAGTTGCAAACAACTACCATGGTGGTAAACTGCCTGCTGGAAAGAACA

TATACAGGATGAGATACAGCTGTGAGCTGGAACAGGCTGCTATTGATGCT

AGTCAAACCTTCTGTTCCGCATCATTGGAGGAACCACAGAAATATGGACA

AAACATCCAAGCATACGTCACACCATCTATAATCGCTCGCCCGAAAAACG

ACCTTCTTGAAGATGCAGTGAAACAATGGTATCTGCCTGTTATCTACTAC

GGCCAACGCGACGCGGCCAACAAGTTCACCGATCCGCGCTTGTACACATT

TGCAAACCTCGCCTACGACAAGAACACTGCACTTGGCTGTCACTATGCGA

AATGTCAAGGCCCTGACAGAATCGTCATTAGTTGCATGTACAACAACGTC

GTTCCTGACAACGCTGTGATCTACGAGCCAGGAACTGCTTGCGTAAAAGA

TCAGGACTGCACTACTTATCCTCAGTCCACATGCAAGGACAGCCTTTGCA

TTATTCCTACGCCACATCCACCAAATCCACCAAATCCACCACCTGCAATG

TGTCCAAACGCTGAAATGACTGATGCAGCACGAAAGAAGGTCCTCGACAT

GCACAACTGGCGCAGATCGCAGCTCGCTCTGGGAAACGTTCAAAACGGGA

AAAATGCTTACAACTGCCCCACTGCAACAGACATGTACAAGATGGAATAT

GATTGCGACCTCGAGAACAGCGCTCTAGCGTATGCAAAGCAATGTAGTCT

CGTTGGTTCAGCAGAAGGAACTCGTCCAGGAGAAGGCGAGAATGTCCACA

AAGGCGCTCTCGTAACCGATCCGGAGGCTGCAGTTCAGACCGCAGTTCAA

GCATGGTGGAGTCAAATCTCACAAAATGGACTCAATGCACAGATGAAATT

CACTGCTTTCTTGAAGGACAAGCCTGACGCTCCGACAGCGTTTACACAGA

TGGCGTGGGCCAAATCCGTAAAGCTTGGATGTGCTGTCTCTAATTGTCAG

GCAGATACCTTCACCGTCTGTAGATACAAAGCTGCCGGAAACATCGTGGG

CGAATTCATCTATACCAAGGGAAATGTATGCGACGCCTGTAAAGCCACAT

GCATTACCGCGGAAGGTCTTTGCCCAACGCCTTGAGCGGCCGC

The first 114 nucleic acids of SEQ ID NO:1 are derived from a cloning vector, and the skilled artisan will appreciate that this portion can be omitted or substituted with other suitable sequences.

The polypeptide encoded by SEQ ID NO:1 has the following amino acid sequence:

(SEQ ID NO: 3)
MGSSHHHHHHSSGLVPRGSHMASMTGGQQMGRGSEFELTTCPGNDLTDAE

RTLLTRVHNSIRREIAQGVANNYHGGKLPAGKNIYRMRYSCELEQAAIDA

SQTFCSASLEEPQKYGQNIQAYVTPSIIARPKNDLLEDAVKQWYLPVIYY

GQRDAANKFTDPRLYTFANLAYDKNTALGCHYAKCQGPDRIVISCMYNNV

VPDNAVIYEPGTACVKDQDCTTYPQSTCKDSLCIIPTPHPPNPPNPPPAM

CPNAEMTDAARKKVLDMHNWRRSQLALGNVQNGKNAYNCPTATDMYKMEY

-continued
DCDLENSALAYAKQCSLVGSAEGTRPGEGENVHKGALVTDPEAAVQTAVQ

AWWSQISQNGLNAQMKFTAFLKDKPDAPTAFTQMAWAKSVKLGCAVSNCQ

ADTFTVCRYKAAGNIVGEFIYTKGNVCDACKATCITAEGLCPTP.

The first 38 amino acids of SEQ ID NO:3 are derived from a cloning vector, and the skilled artisan will appreciate that this portion can be omitted or substituted with other suitable fusion partners.

In an effort to identify tools for capturing and detecting hookworm and/or hookworm antigen in hookworm-infected mammals, the present inventors have determined that only a truncated portion (about 28 kDa) of the full-length (56 kDa) protein, and therefore not the 56 kDa version, is present in the feces of canines that are infected by *Ancylostoma*. (This 28 kDa truncated portion of ASP5 is referred to herein as "CoproASP5"; the detection of CoproASP5 in feces of *Ancylostoma*-infected canines is described in the Example section included herein.) In one aspect, therefore, the present invention provides polypeptides that may be used to generate antibodies that may be used to robustly capture and detect CoproASP5. One such polypeptide that may be used to generate antibodies that may be used to bind CoproASP5 is referred to as ASP5-1 polypeptide, which may be encoded by the following nucleic acid sequence:

(SEQ ID NO: 2)
ATGGGCAGCAGCCATCATCATCATCATCACAGCAGCGGCCTGGTGCCGCG

CGGCAGCCATATGGCTAGCATGACTGGTGGACAGCAAATGGGTCGCGGAT

CCGAATTCGAGCTCACCACTTGTCCAGGAAATGATCTAACAGATGCTGAA

CGCACACTGCTAACTAGGGTGCACAATTCCATTCGACGGGAAATAGCGCA

AGGAGTTGCAAACAACTACCATGGTGGTAAACTGCCTGCTGGAAAGAACA

TATACAGGATGAGATACAGCTGTGAGCTGGAACAGGCTGCTATTGATGCT

AGTCAAACCTTCTGTTCCGCATCATTGGAGGAACCACAGAAATATGGACA

AAACATCCAAGCATACGTCACACCATCTATAATCGCTCGCCCGAAAAACG

ACCTTCTTGAAGATGCAGTGAAACAATGGTATCTGCCTGTTATCTACTAC

GGCCAGCGCGACGCGGCCAACAAGTTTACGGATCCGCGCTTGTACACATT

TGCAAACCTCGCCTACGACAAGAACACTGCACTTGGCTGTCACTATGCGA

AATGTCAAGGCCCTGACAGAATCGTCATTAGTTGCATGTACAACAACGTC

GTTCCTGACAACGCAGTGATCTACGAGCCTGGAACTGCTTGCGTAAAAGA

TGCGGACTGCACTACTTATCCTCAGTCCACATGCAAGGACAGCCTTTGCA

TTATTCCTACGCCACATCCACCAAATCCACCAAATCCACCACCAGCAATG

AGTCCATGAGCGGCCGC

A skilled artisan will appreciate that due to the degeneracy of the genetic code, nucleic acid sequences other than SEQ ID NO:2 can code for the polypeptide of SEQ NO:4 if appropriate (silent) codon substitutions are made.

The corresponding ASP5-1 polypeptide has the following amino acid sequence:

(SEQ ID NO: 4)
MGSSHHHHHHSSGLVPRGSHMASMTGGQQMGRGSEFELTTCPGNDLTDAE

RTLLTRVHNSIRREIAQGVANNYHGGKLPAGKNIYRMRYSCELEQAAIDA

```
                    -continued
SQTFCSASLEEPQKYGQNIQAYVTPSIIARPKNDLLEDAVKQWYLPVIYY

GQRDAANKFTDPRLYTFANLAYDKNTALGCHYAKCQGPDRIVISCMYNNV

VPDNAVIYEPGTACVKDADCTTYPQSTCKDSLCIIPTPHPPNPPNPPNPP

PAMSP
```

In one embodiment, the polypeptide of the invention includes an amino acid sequence that is identical to or is homologous to a sequence represented by SEQ ID NO:4. An exemplary method for creating the polypeptide having SEQ ID NO.:4, which includes amino acid sequence derived from vector and also includes amino acid sequence derived from *Ancylostoma caninum*, is described in the Example section included herein.

Because the first 38 amino acid residues of the polypeptide having the amino acid sequence that corresponds to SEQ ID NO:4 were not derived from *Ancylostoma* (i.e., they are vector sequence), it is further contemplated that the peptide of the present invention may include an amino acid sequence that is identical to or is homologous to a sequence represented by SEQ ID NO:4, wherein the X at position 1 is M or absent, the X at position 2 is G or absent, the X at position 3 is S or absent, the X at position 4 is S or absent, the X at position 5 is H or absent, the X at position 6 is H or absent, the X at position 7 is H or absent, the X at position 8 is H or absent, the X at position 9 is H or absent, the X at position 10 is H or absent, the X at position 11 is S or absent, the X at position 12 is S or absent, the X at position 13 is G or absent, the X at position 14 is L or absent, the X at position 15 is V or absent, the X at position 16 is P or absent, the X at position 17 is R or absent, the X at position 18 is C or absent, the X at position 19 is S or absent, the X at position 20 is H or absent, the X at position 21 is M or absent, the X at position 22 is A or absent, the X at position 23 is S or absent, the X at position 24 is M or absent, the X at position 25 is T or absent, the X at position 26 is G or absent, the X at position 27 is G or absent, the X at position 28 is Q or absent, the X at position 29 is Q or absent, the X at position 30 is M or absent, the X at position 31 is G or absent, the X at position 32 is R or absent, the X at position 33 is G or absent, the X at position 34 is S or absent, the X at position 35 is E of absent, the X at position 36 is F or absent, the X at position 37 is E or absent, and the X at position 38 is L or absent. Furthermore, because the S at position 251 in the SEQ ID NO:3 was artificially substituted during the cloning process described in the Example section herein in that sequence (the ASP5 protein of wild-type *Ancylostoma* includes a C residue at that position), it is contemplated that the X at position 251 of SEQ ID NO:4 may be either S or C.

The polypeptides of the present invention are capable of eliciting an immune response in a host animal that is exposed to these polypeptides to produce one or more of the antibodies of the present invention. Regardless of the technique by which they are derived, the polypeptides of the present invention are preferably prepared in substantially pure form when they are to be used for the purpose of raising antibody. Preferably, these polypeptides are at least about 80% pure, more preferably are at least about 90-95% pure, and even more preferably are at least about 99% pure. Exemplary techniques for an immune response in a host organism and for isolating antibodies therefrom are described herein, but it is to be understood that the present invention is not limited to those techniques. The skilled artisan will recognize that there are a plurality of techniques for achieving this same goal without deviating from the scope and spirit of the invention.

II. Antibodies of the Invention

The present invention further includes antibodies and antigen-binding fragments thereof that are raised against and that specifically bind all or part of one or more polypeptides of the present invention, and also includes compositions that include said antibodies and antigen-binding fragments thereof. When contacted to a sample obtained from a mammal, these antibodies and antigen-binding fragments are able to specifically bind hookworm antigen present in the sample, but are not able to specifically bind any antigen from roundworm, whipworm, or heartworm that may be present in the sample. The antibodies of the present invention are suitable for being used only to capture one or more hookworm antigens, only to detect one or more hookworm antigens, or more preferably, to both capture and detect one or more hookworm antigens. The hookworm antigen that is captured and/or detected may be, but is not limited to being, CoproASP5.

The antibodies of the present invention may belong to any antibody class, including for example, IgG, IgM, IgA, IgD and IgE, and may be prepared by any of a variety of techniques known to the skilled artisan. (See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994): Drenckhahn et al. *Methods Cell. Biol.* 37:7-56 (1993): Morrison, *Ann. Rev. Immunol.* 10:239-65 (1992); Wright et al. *Crit. Rev. Immunol.* 12:125-68 (1992); Harlow and Lane, *Antibodies: A Laboratory Manual*, Cold Spring Harbor Laboratory (1988); and *Making and Using Antibodies: A Practical Handbook*, Howard and Kaser, eds., CRC Press (2006), each one of which is incorporated herein by reference in its entirety.)

In one technique, the polypeptide of the invention is introduced into a host animal, such as into rabbit, mouse, rat, guinea pig, goat, pig, cow, sheep, donkey, dog, cat, chicken, or horse, for example. An enhanced immune response may be elicited in the host animal by associating the polypeptide with a carrier and/or by exposing the host to an adjuvant, but it is to be understood that the present invention does not require that the polypeptide be associated with a carrier or that the host be exposed to the adjuvant. An exemplary carrier that may be used for this purpose is bovine serum albumin, bovine thyroglobulin, and soybean trypsin inhibitor. Exemplary adjuvants include Freund's complete or incomplete adjuvant and MDL-TDM adjuvant. Regardless of whether the polypeptide is associated with such a carrier or whether the host is exposed to an adjuvant, booster immunizations optionally may be made with the host animal being bled one or more times thereafter. Polyclonal antibodies that specifically bind the polypeptide may then be purified from antisera obtained from the bleed or bleeds. Such purification may be achieved, for example, by employing affinity chromatography techniques that involve associating the polypeptide to a solid support. Such affinity chromatography techniques are well known by the skilled artisan.

In one embodiment, the antibody of the present invention is an antibody that is raised in rabbit by immunizing that host animal with the polypeptide having the amino acid sequence corresponding to SEQ ID NO.:4. (Hereinafter, this particular antibody is referred to as "anti ASP5-1 pAB".) A specific technique for producing and isolating this antibody is described in the Example section included herein, but the skilled artisan will recognize that the production and isolating of anti-ASP5-1 pAB, or any other antibody of the present invention, is not limited to that specific technique.

In other embodiments, the antibody of the present invention is raised in a host against one or more polypeptides having an amino acid sequence that is a conservative variant of the sequence corresponding to SEQ ID NO:3. In some other embodiments, the antibody of the present invention is raised in a host against any one or more polypeptides having an amino acid sequence corresponding to the sequence of SEQ ID NO:4, or one or more polypeptides having an amino acid sequence that is a conservative variant of any of that sequence.

It is also to be understood that the antibodies of the invention optionally may be polyclonal antibodies, monoclonal antibodies, single chain antibodies (scFv) chimeric antibodies, and fragments thereof. Monoclonal antibodies that are specific for the polypeptide of interest, such as that having sequence identical or homologous to SEQ ID NO:3 or SEQ ID NO:4, for example, may be obtained and purified, for example, by preparing cell lines that generate antibodies having the desired specificity to the polypeptide of interest. Cell lines of this kind may be derived from cells of a particular type (e.g., spleen cells) that are isolated from a host animal that had previously been immunized with the polypeptide as described before. In such a case, these cells could then be immortalized, for example, by fusing them with myeloma cells by carrying out any one of a variety of fusion techniques known to the skilled artisan. In one exemplary technique, the cells from the immunized host animal are co-incubated with their fusion partner, e.g., the myeloma cells, in the presence of a detergent for a short period of time before being plated on a medium that supports the growth of hybrid cells (but not the myeloma fusion partner). Such selection may be achieved, for example, by using hypoxanthine, aminopterin, and thymidine (HAT). When hybrid cells emerge during selection, in perhaps one or two weeks after commencing the selection process, single hybrid colonies (and their supernatants) are tested for their ability to bind the polypeptide or polypeptides against which the host animal was immunized. Hybrid colonies having the most optimal binding specificity would represent the best candidates from which monoclonal antibodies may be isolated. These monoclonal antibodies, for example, may be isolated directly from the supernatant (i.e., medium) in which these colonies are grown by employing any one of a variety techniques known to the skilled artisan.

The antibody of the invention also may be a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, $F(ab')_2$ and $F_v$ fragments. In addition to production and purification from animals or mammalian cells, antibodies, antibody fragments, or non-antibody scaffolds can be selected based upon various in vitro technologies, including phage display, ribosomal display, or bacterial display.

Antibodies, including secondary antibodies, may be labeled with any type of label known in the art, including, for example, fluorescent, chemiluminescent, radioactive, enzymes, colloidal particles, radioisotopes and bioluminescent labels. In various embodiments of the invention, the one or more of the antibodies of the invention are labeled with an enzyme, a colloidal particle, a radionuclide or a fluorophor. The particulate label can be, for example, a colored latex particle, dye sol, or gold sol conjugated to an antibody.

III. Methods, Devices and Kits of the Invention

Devices and Kits of the Invention

The present invention, in one aspect, is a device for the detection of hookworm infection in a mammal, such as a canine, feline, porcine, bovine, or human, for example. The device is arranged to aid in the detection of the presence or absence of hookworm antigen, such as CoproASP5, for example, in a sample from a mammal that may also be infected with one or more other worm parasites, including roundworm, whipworm, and heartworm.

In one aspect, the device includes a solid support, wherein one or more antibodies of the invention are immobilized on the solid support. The solid support may be, but is not limited to being, the inner, bottom surface of a well of a microtiter plate or a substrate that is included as part of a lateral flow device, for example. An exemplary microtiter plate is an IMMULON® 1B 96-well plate (which is commercially available from Thermo Scientific of Milford, Mass.), but it is to be understood that the skilled artisan will recognize that a large variety of other microtiter plates that are not the IMMULON® 1B 96-well plate allow for the immobilization of antibodies thereon, and therefore would be suitable for providing the solid support of the present invention.

An exemplary lateral flow device is the lateral flow device that is described in U.S. Pat. No. 5,726,010, which is incorporated herein by reference in its entirety. The device for performing a lateral flow assay may be a SNAP® device, which is commercially available from IDEXX Laboratories, Inc. of Westbrook, Me. However, it is to be understood that the skilled artisan will recognize that a large variety of other lateral flow devices that are not SNAP® devices or described by U.S. Pat. No. 5,726,010 allow for the immobilization of an antibody thereon, and therefore would be suitable for being used as the device of the present invention. These devices can include, for example, lateral flow devices that use colloidal gold technology.

Antibodies used in the device of the invention may be immobilized on the solid support by any methodology known in the art, including, for example, covalently or non-covalently, directly or indirectly, attaching the antibodies to the solid support. Therefore, while these antibodies may be attached to the solid support by physical adsorption (i.e., without the use of chemical linkers), it is also true that these antibodies may be immobilized to the solid support by any chemical binding (i.e., with the use of chemical linkers) method readily known to one of skill in the art.

It is also to be understood that the solid support may be any suitable material for the immobilization of the antibodies of the invention. For example, the solid support may be beads, particles, tubes, wells, probes, dipsticks, pipette tips, slides, fibers, membranes, papers, natural and modified celluloses, polyacrylamides, agaroses, glass, polypropylene, polyethylene, polystyrene, dextran, nylon, amylases, plastics, magnetite or any other suitable material readily known to one of skill in the art.

The device optionally may include one or more labeled antigen capture reagents that may be mixed with a test sample prior to application to a device of the invention. When the labeled capture antigen reagent is included, the labeled antigen capture reagent may or may not be deposited or dried on a solid surface of the device. "Antigen capture reagent" refers to any compound that is specific for the antigen or antigens of interest. The labeled antigen capture reagent, whether added to the mammalian sample or predeposited on the device, may be, for example, a labeled antibody specific for a hookworm antigen, including, but not limited to, the antibodies of the present invention. In just one example, anti-ASP5-1 pAB conjugated with horseradish peroxidase may be used as a labeled antigen capture reagent.

The device also may optionally include a liquid reagent that transports (such as when the device is a SNAP® device, for example), or otherwise facilitates removal of (such as when the device includes a microliter plate, for example), unbound material (e.g., unreacted portions of the mammalian sample, such as, for example, unreacted portions of fecal extract, and unbound antigen capture reagent) away from the reaction zone (solid phase). The liquid reagent may be a wash reagent and serve only to remove unbound material from the reaction zone, or it may include a detector reagent and serve to both remove unbound material and facilitate antigen detection. For example, in the case of an antigen capture reagent conjugated to an enzyme, the detector reagent includes a substrate that produces a detectable signal upon reaction with the enzyme-antibody conjugate at the reaction zone (solid phase). Alternatively, in the case of a labeled antigen capture reagent conjugated to a radioactive, fluorescent, or light-absorbing molecule, the liquid reagent acts merely as a wash solution facilitating detection of complex formation at the reactive zone by washing away unbound labeled reagent.

The liquid reagent may further include a limited quantity of an "inhibitor", i.e., a substance that blocks the development of the detectable end product. A limited quantity is defined as being an amount of inhibitor sufficient to block end product development until most or all excess, unbound material is transported away from the second region, at Which time detectable end product is produced.

The device of the present invention may also include various binding reagents immobilized at locations distinct from the antigen capture reagent or reagents. For example, an immunoreagent (an antibody, antigen or polypeptide) that recognizes a species-specific (e.g., hooky corm-specific) antibody portion of a labeled antibody or antigen capture reagent, or an enzyme portion of an enzyme-labeled reagent, can be included as a positive control to assess the viability of the reagents within the device. For example, a positive control may be an anti-horseradish peroxidase antibody that has been raised in, for example, goat or mouse. Additionally, a reagent, e.g., an antibody, isolated from a non-immune member of the species from which the antibody portion of the antigen-antibody complex was derived can be included as a negative control to assess the specificity of immunocomplex (i.e., antigen-antibody complex) formation.

In addition to being designed to detect hookworm in a test sample, the device of the invention optionally may be designed to allow one or more other diagnostic tests to be performed. For example, the solid support may also include reagents for the detection of one or more non-hookworm worm parasites, one or more non-worm parasites, one or more viruses, one or more fungi, or one or more bacteria. The reagents for the detection of one or more non-hookworm worm parasites, one or more non-worm parasites, one or more viruses, one or more fungi, or one or more bacteria may be, for example, one or more antibodies or one or, more antigens recognized by antibodies specific for one or more non-hookworm worm parasites, one or more non-worm parasites, one or more viruses, one or more fungi, or one or more bacteria.

In one embodiment the device of the present invention is a microtiter plate that includes a plurality of wells, wherein each well includes a solid support having anti-ASP5-1 pAB immobilized thereupon.

The plate may be used in conjunction with a method of the present invention to detect hookworm in a test sample. Specifically, a hookworm infection may be diagnosed in a mammal by detecting one or more hookworm antigens with the anti-ASP5-1 pAB that is immobilized on the solid support. In one embodiment, the antigens that are detected are hookworm coproantigens. "Hookworm coproantigens" are any product or products of hookworm that are present in a fecal sample and that can specifically and stably bind to the anti-ASP5-1 pAB. Hookworm coproantigens therefore may be whole hookworm, hookworm eggs, hookworm fragments, or products secreted, excreted or shed from hookworm or a combination thereof. Hookworm coproantigens further include the polypeptides of the present invention, such as the polypeptides having an amino acid sequence corresponding to SEQ. ID NOS:3 AND 4, polypeptides having an amino acid sequence that is a conservative variant of those sequences, and/or antigenic fragments of any such polypeptides, for example. An exemplary hookworm coproantigen is CoproASP5 that was detected by the present inventors in fecal samples obtained from hookworm-infected canines as described herein.

The invention further includes assay kits (e.g., articles of manufacture) for detecting hookworm in a test sample. A kit therefore may include one or more devices and/or compositions of the present invention. For example, the kit may include anti-hookworm antibodies and means for determining binding of the antibodies to hookworm antigens in the sample. In one particular example, such a kit includes the device having an immobilized anti-hookworm antibody, such as anti-ASP5-1 pAB, for example, one or more antigen capture reagents (e.g., a non-immobilized labeled antigen capture reagent and an immobilized antigen capture reagent) and wash reagent, as well as detector reagent and positive and negative control reagents, if desired or appropriate. Other components such as buffers, controls, and the like, known to those of ordinary skill in art, may be included in such test kits. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample. The present kit may further include instructions for carrying out one or more methods of the present invention, including instructions for using any device and/or composition of the present invention that is included with the kit.

B. Methods of the Invention

The present invention further includes methods for using one or more of the devices, kits and/or compositions of the present invention to detect the presence or absence of hookworm in a test sample. The methods therefore may be carried out to detect the presence or absence of hookworm in a sample, such as, for example, a fecal, sample, that is obtained from a mammal, including, but not limited to, a canine, feline, porcine, bovine or human. Furthermore, the methods may be carried out to detect *Ancylostoma*, such as *Ancylostoma caninum, Ancylostoma braziliense, Ancylostoma duodenal, Ancylostoma ceylanicum, Ancylostoma tubaeforme* or *Ancylostoma pluridentatum*, for example. It is to be understood, however, that these methods are not limited to being used to detect *Ancylostoma*, and therefore these methods may be carried out for the purpose of detecting other species of hookworm, such as *Necator* and/or *Uncinaria*, including *Necator americanus* and *Uncinaria stenocephala*, for example. These methods further are useful for confirming such presence or absence of hookworm in a sample even when that sample includes one or more products derived from other worm species, including one or more products from roundworm, whipworm, and/or heartworm.

In the methods of the present invention, detection of hookworm may be accomplished by detecting the presence or absence of one or more hookworm antigens, such as the polypeptides having an amino acid sequence corresponding to SEQ ID NOS:1 AND 2, as well as antigenic fragments and/or conservative variants of those sequences, for example. When the sample under test for hookworm is feces, the soluble portion of the feces may be collected by any protocol known in art. For example, in addition to the specific protocol described in the Example section herein, the soluble portions of the sample generally may be collected by using filtration, extraction, centrifugation, or simple mixing followed by gravimetric settling. The skilled artisan will recognize that there are a variety of ways of extracting and preparing non-fecal samples from a mammal as well. For example, the sample may be a bodily fluid that is naturally excreted or otherwise released by the mammal or that is artificially obtained from the mammal. Such artificial extraction may be carried out by milking the mammal or by injecting a syringe into the mammal and drawing the fluid into the syringe. Once obtained, the fluid optionally may be fractionated (for example, serum may be fractionated from whole blood as then used as the sample). As another example, the sample may be obtained by swabbing the mammal, such as the oral cavity of the mammal, for example. As a third example, the sample may be obtained from the digestive tract mucous. As yet another example, tissue sections may be obtained by biopsy.

The methods include contacting the test sample with one or more antibodies specific for one or more hookworm antigens under conditions that allow an antigen/antibody complex, i.e., an immunocomplex, to form. That is, an antibody specifically hinds to a hookworm antigen present in the sample. The skilled artisan is familiar with assays and conditions that may be used to detect such antigen/antibody complex binding. For example, the antigen/antibody complex may be detected using a secondary antibody that binds to the antigen/antibody complex. The formation of a complex between hookworm antigen and anti-hookworm antibodies in the sample may be detected using any suitable method known in the art.

Furthermore, the relative amount of antibody-antigen complexes that are formed in one particular reaction may be measured with respect to those formed in any other reaction by any methodology known in the art for achieving that goal. When it is determined that a sample under test has more antibody-antigen complexes than does a control sample, it can be concluded that hookworm is present in the test sample. When this is true, it may be concluded that the mammal from which the test sample was obtained harbors an intestinal hookworm infection. Either one or both of the conclusions that hookworm is present in the test sample and that the mammal being tested harbors an intestinal hookworm infection may be made by a clinician at a diagnostic service provider or by a caregiver of the mammal, such as the mammal's veterinarian, for example. When a caregiver of a mammal determines (or is otherwise informed that) a mammal harbors a hookworm infection, the caregiver may then subject the mammal to a course of treatment that is optimally designed to rid the mammal of hookworm specifically, rather than of a parasitic nematode infection generally. In addition, humans who may come in contact with the infested animal or its excretions may be advised to take precautions against acquiring the parasite. In this context, it is important to determine the worm species with high specificity, as some helminths, such as hookworms and roundworms, can cause significant disease (e.g., larval migrans) in humans, while it is generally accepted that whipworm does not play a zoonotic role of importance in humans. Furthermore, the present invention can be used to confirm that any animal that has received treatment for a hookworm infection has been rid of that infection.

The steps of the method of the present invention may include applying a test sample to a device of the invention, which includes an immobilized antibody specific for one or more hookworm antigens, and detecting the presence or absence of the hookworm antigen in the sample. Antibodies specific for antigens of hookworms may be directly or indirectly attached to a solid support or a substrate such as a microtiter well, antibody-immobilizing portion of a SNAP® device, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). All of these substrate materials may be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

The methods of the present invention do not require the use of solid phases or substrates, however. The skilled artisan will recognize that there are a number of ways that the present method may be carried out to detect the presence or absence of hookworm without involving the use of solid phases or substrates. In just one example, immunoprecipitation methods that do not require the use of solid phases or substrates may be carried out.

In some embodiments of the invention, the antigen/antibody complex is detected when an indicator reagent, such as an enzyme conjugate, which is bound to the antibody, catalyzes a detectable reaction. Optionally, an indicator reagent including a signal generating compound may be applied to the antigen/antibody complex under conditions that allow formation of a detectable antigen/antibody/indicator complex. Optionally, the antibody may be labeled with an indicator reagent prior to the formation of an antigen/antibody complex.

The formation of an antigen/antibody complex or an antigen/antibody/indicator complex in some of the methods of the present invention specifically may be detected by radiometric, colorimetric, fluorometric, photometric, size-separation, or precipitation methods. Detection of an antigen/antibody complex also may be accomplished by the addition of a secondary antibody that is coupled to an indicator reagent including a signal generating compound. Indicator reagents including signal generating compounds (labels) associated with a polypeptide/antibody complex may be detected using the methods described above and may include chromogenic agents, catalysts such as enzyme conjugates, fluorescent compounds such as fluorescein and rhodamine, chemiluminescent compounds, such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Methods of the invention include, but are not limited to those based on competition, direct reaction or sandwich-type assays, including, but not limited to Western blots, ELISA, RIA, immuno-fluorescent assays (IFA), hemagglutination (HA), fluorescence polarization immunoassay (FPIA), and microtiter plate assays (i.e., any assay done in one or more wells of a microliter plate). One assay of the invention includes a reversible flow chromatographic binding assay, which may be performed, for example, by using a SNAP® device. See U.S. Pat. No. 5,726,010.

In some embodiments, the method of the invention facilitates sandwich or competition-type specific binding assays. In a sandwich assay, antigen capture reagents are immobilized in a reactive zone. These antigen capture reagents may specifically bind to antigens in the sample being tested for hookworm. Following binding of the antigen from the sample, the antigen capture reagent/antigen complex is detected by any suitable method. For example, the complex may be reacted with labeled specific binding reagents (e.g., an enzyme-antibody conjugate) and antigen detected (e.g., upon reaction with substrate).

In other embodiments of the method of the present invention, a competition assay is performed. In a competition assay, antigen capture reagents are immobilized at the reactive zone and are contacted simultaneously with antigen from a sample and labeled antigen (e.g., an antigen-enzyme conjugate). The amount of label detected at the reactive zone is inversely proportional to the amount of antigen in the sample.

In some embodiments of the method, antibodies specific for a hookworm antigen or antigens are attached to a solid phase or substrate. A sample potentially including au antigen from hookworm is added to the substrate. Antibodies that specifically bind hookworm are added. The antibodies may be the same antibodies used on the solid phase or they may be from a different source or species. Furthermore, these antibodies may be linked to an indicator reagent, such as an enzyme conjugate. Wash steps may be performed prior to each addition. A chromophore or enzyme substrate may be added and color may be allowed to develop. The color reaction may be stopped and the color may be quantified using, for example, a spectrophotometer, and/or the color may be subjectively assessed by the human eye.

In other embodiments of the method, antibodies specific for a hookworm antigen or antigens are attached to a solid phase or substrate. A sample potentially including a hookworm antigen is added to the substrate. Second anti-species antibodies that specifically bind antigens of hookworms are added. These second antibodies are from a different species than are the solid phase antibodies. Third anti-species antibodies that specifically bind the second antibodies and that do not specifically bind the solid phase antibodies are added. The third antibodies may include an indicator reagent, such as an enzyme conjugate. Wash steps may be performed prior to each addition. A chromophore or enzyme substrate may added and color may be allowed to develop. The color reaction may be stopped and the color may be quantified using, for example, a spectrophotometer, and/or the color may be subjectively assessed by the human eye.

In a specific example, the method of the present invention is performed in conjunction with a device that is a lateral flow assay device by adding a prepared mammalian fecal extract sample to a flow matrix of the device at a first region (a sample application zone). The prepared sample is carried in a fluid flow path by capillary action to a second region of the flow matrix where a particulate label capable of binding and forming a first complex with an antigen in the sample exists. The particulate label can be, e.g., a colored latex particle, dye sol, or gold sol conjugated to an antibody specific for a hookworm antigen. The first complex is carried to a third region of the flow matrix where an antibody that specifically binds a hookworm antigen is immobilized at a distinct location. A second complex is formed between the immobilized antibody and the first complex. The particulate label that is part of the second complex can be directly visualized by the human eye.

Hookworm antibody may be an immobilized antigen capture reagent in a reaction zone (solid phase). A second antigen capture reagent, a second hookworm antibody that has been conjugated to a label, either may be added to the sample before the sample is added to the device, or the second antigen capture reagent can be incorporated into the device. For example, the labeled antigen capture reagent may be deposited and dried on a fluid flow path that provides fluid communication between a sample application zone and the solid phase. Contact of the labeled antigen capture reagent with the test sample can result in dissolution of the labeled antigen capture reagent.

In one embodiment of the method of the present invention, hookworm antigen is detected by ELISA. Specific examples of the ELISA method of the present invention is described in the Example section included herein. Although the present invention is described with respect to those specific ELISA methods, however, it is to be understood that those of ordinary skill in the art will recognize that alternative, additional or substitute ELISA steps may be used without deviating from the basic goal achieved through this method of the invention.

In another embodiment of the present invention, hookworm antigen is detected by using a lateral flow device, such as a SNAP® device, for example.

Furthermore, the methods of the invention for detection of hookworm infection can be combined with other diagnostic assays to detect the presence of other organisms or conditions. For example, assays of the invention can be combined with reagents that detect one or more non-hookworm worm fecal parasites, one or more non-worm fetal parasites, one or more viruses, one or more fungi, one or More bacteria, one or more blood-borne parasites or occult blood or a combination thereof. By providing two or more unique binding sites in a single assay device (such as, for example, two unique spots on a SNAP® assay device), the present invention allows for detection of two or Mote organisms from a single sample. In one embodiment, there are three unique spots for detection of past or present infection or infestation from three organisms (the spots being either antigen or antibody binding reagents) from a single sample (i.e., the same individual sample is exposed to the three capture reagents on a single device). In yet another embodiment, there are four unique spots for detection of past or present infection or infestation from four organisms (the spots being either antigen or antibody binding reagents) from a single sample (i.e., the same individual sample is exposed to the four capture reagents on a single device. It is to be understood, however, that the same device may include more than four unique spots and/or allow for the detection of more than four organisms.

The reagents for the detection of one or more non-hookworm worm parasites, one or more non-worm parasites, one or more viruses, one or more fungi, or one or more bacteria may be, for example, one or more antibodies or one or more antigens recognized by antibodies specific for one or more non-hookworm worm parasites, one or more non-worm parasites, one or more: viruses, one or more fungi, or one or more bacteria.

When a device of the present invention includes reagents for the specific detection of roundworm and reagents for the specific detection whipworm, for example, in addition to the reagents for detecting hookworm, the method of the present invention may involve using that device for the additional purpose or purposes of determining whether the sample that is being tested for hookworm also includes roundworm and/or whipworm. See U.S. Provisional Application Ser. No. 61/122,260 entitled "Methods, Devices, Kits and Compositions for Detecting Roundworm, Whipworm, and Hookworm," filed Dec. 12, 2008, which is incorporated by reference in its entirety. In this arrangement, therefore, the method/device of the present invention would not only be able to specifically confirm that hookworm is present in or absent from any particular test sample, but it would also be useful for specifically confirming that the sample includes or does not include any antigen of roundworm and/or any antigen of whipworm. The capability to specifically detect hookworm and one or more other organisms by applying a single sample to the device, of the invention would be useful to the caregiver of the animal from which the sample under test was obtained. A caregiver who learns that a sample includes both hookworm and whipworm, but not roundworm, for example, could use that knowledge to treat the mammal from which the sample was taken specifically for roundworm by administering to that mammal a drug optimally effective against hookworm and a second drug optimally effective against whipworm. Absent such knowledge, the caregiver may, for example, otherwise treat the mammal with a drug that is optimally effective against only hookworm, only whipworm, or neither hookworm nor whipworm (in such cases, the mammal would be at risk of receiving suboptimal treatment). In addition, humans who may come in contact with the infested animal or its excretions may be advised to take precautions against acquiring the parasite or parasites. In this context, it is important to determine the worm species with high specificity, as some helminths, such as hookworms and roundworms, can cause significant disease (i.e., larva migrans) in humans, while it is generally accepted that whipworm does not play a zoonotic role of importance in humans.

The method further may optionally include using one or more nucleic acids from hookworm to help confirm the presence or absence of hookworm in a test sample. Such use of these nucleic acids for determining the presence of hookworm may be carried out before, after or concomitantly with the carrying out of any other aspects of the method, including the detection of hookworm by antibody. Therefore, in one aspect, after hookworm is detected or not detected in a particular sample and the mammal from which the sample was obtained is diagnosed as either having or not having a hookworm infection, the sample (or a later-obtained sample from the diagnosed mammal) may be tested for the presence or absence of any one or more hookworm-specific nucleic acids. Anyone failing to detect hookworm in a particular mammal by using one or more nucleic acids (after the hookworm had been detected by using one or more antibodies) would need to take into consideration the possibility that the antibodies had detected hookworm antigen prior to the appearance of detectable hookworm nucleic acid in the sample. In such an instance, the mammal's caregiver may elect to ignore the observation that the nucleic acid had failed to detect the hookworm and proceed with treating the mammal specifically for hookworm infection based on the observation that the antibodies had in fact detected hookworm.

In another aspect, nucleic acids are used to determine the presence or absence of hookworm in a particular mammal, and then the presence or absence of hookworm is further evaluated by using the antibodies of the present invention. Detection of one or more hookworm nucleic acids may be carried out by using any nucleic acid detection techniques known to the skilled artisan. For example, such detection may be carried out by performing a PCR-based technique, such as, but limited to, for example, a real-time PCR-based technique. Exemplary PCR-based techniques are described in, e.g., *PCR Protocols* (*Methods in Molecular Biology*), $2^{nd}$ ed., Bartlett and Stirling, eds., Humana Press (2003); and Sambrook and Russell, *Molecular Cloning: A Laboratory Manual*, Cold Spring Harbor Laboratory Press (2001); each one of which is incorporated herein by reference in its entirety.

The present invention is specifically described with reference to certain Examples; however, it is not to be construed as being limited thereto.

Example 1

A Novel Isoform of ASP5, Which is Herein Referred to as CoproASP5, is Present in Feces of Canines That are Infected with *Ancylostoma*

Canine fecal sample preparation. Canine animals known to harbor a hookworm (*Ancylostoma caninum*) infection or to not have a parasitic worm infection provided the source of fecal samples. A sample (approximately 1 gram) of frozen, unpreserved canine feces pooled from five hookworm-infected or uninfected canines was suspended in 4 ml of extraction buffer ("extraction buffer" is 1× phosphate-buffered saline (PBS), pH 7.0-7.5 with 0.05% TWEEN® 20). This suspension was vortexed for 2 minutes and then was centrifuged at 13,000 rpm for 25 minutes to produce a first supernatant. This first supernatant was then centrifuged at 10,000 rpm for 5 minutes to produce a second supernatant. This second supernatant hereinafter is referred to as "fecal extract".

Ion-exchange chromatography. Ion-exchange chromatography was performed by using HITRAP™ SEPHAROSE™ HP IEX Columns, which are commercially available from GE Healthcare Bio-Sciences Corp. of Piscataway, N.J., according to manufacturer's protocol. Briefly, fecal extract was adjusted to pH 5.0-5.5 with HCl and then flowed over HITRAP™ SP HP column at a flow rate of 2 min. The column was washed with acetic acid buffer, pH 5.0-5.5. The column was eluted with acetic acid buffer, pH 5.0-5.5+1 M NaCl. The eluant was then concentrated using ICON® concentrator, Thermo Scientific, Cat.#89887.

Mass spectroscopy was then performed on the eluant of the ion-exchange chromatography (FIG. 1) using a WATERS® Q-T of ULTIMA® Mass spectrometer (Yale cancer center mass spectrometry resource and the W. M. Keck foundation Biotechnology resource laboratory, New Haven, Conn.). This analysis identified four polypeptide fragments, which positively identified the N-terminal 28 kD band (CoproASP5) as a fragment of ASP5.

Western blot analysis. Western analysis was performed according to protocols that are well known to the skilled artisan. Briefly an 18 µl sample mixture (in each lane 1-X) was separated by molecular weight on a 4-16% SDS-PAGE gradient gel and transferred to a nitrocellulose membrane (FIG. 1). Each sample mixture contained 5 µl 4× NUPAGE® LDS Sample buffer, purchased from Invitrogen (Cat. #NP0007) and 2 µl NUPAGE® Sample reducing agent, purchased from Invitrogen (Cat #NP0004). Lane 1 further contained 13 µl extract of whole hookworm (*Ancylostoma caninum*, purchased from Antibody Systems, Inc. Hurst, Tex. (Cat; 76054); lane 2 further contained 13 µl of "fraction 32" obtained from the hookworm-infected canines in the ion-exchange chromatography experiment; lane 3 further contained 13 µl of "fraction 33" obtained from the hookworm-infected ion-exchange chromatography experiment; lane 4 further contained 13 µl of a first fraction obtained from uninfected canines in the ion-exchange chromatography experiment; lane 5 further contained 13 µl of a second fraction obtained from uninfected canines in the ion-exchange chromatography experiment; lane 6 contained 13 µl of fecal extract (unfractionated) obtained from the hookworm-infected canines; and lane 7 contained 13 µl of fecal extract (unfractionated) obtained from the uninfected canines. (Molecular standards were run in the lane marked "M". Sizes of these molecular standards are indicated.)

Following protein transfer to the membrane, the membrane was probed by using anti-Ac-ASP-5 pAB. ("Anti-Ac-ASP-5 pAB" was raised against ASP5 and isolated as described in U.S. patent application Ser. No. 11/763,583, entitled "Roundworm Coproantigen Detection", filed Jun. 15, 2007, assigned to IDEXX Laboratories, and incorporated herein in its entirety by reference.) The detection antibody was the anti-Ac-ASP-5pAB conjugated to horseradish peroxidase (HRPO). The conjugate was made by labeling reduced IgG pAb with SMCC-HRPO (SMCC is succinimidyl 4-[N-maleimidomethyl]cyclohexane-1-calboxylate).

As shown in FIG. 2, anti-Ac-ASP-5 pAB bound to a product of about 56 kDa in extract of whole hookworm (lane 1; see arrowhead). Furthermore, as shown by the solid arrows, anti-Ac-ASP-5 pAB hybridized to a product of about 28 kDa in the two lanes containing the fecal samples from hookworm-infected canines that were fractionated by ion-exchange chromatography (i.e., lanes 2 and 3), and in the unfractionated fecal sample from hookworm-infected canines (lane 7; see dashed arrow). These data indicate that a truncated version of ASP-5 (of about 28 kDa, herein referred to as CoproASP5) is present in hookworm-infected canines, and is not present in uninfected canines.

Example 2

Antibody Raised Against SEQ ID NO:4 Specifically Binds Coproantigen in Hookworm-infected Canines, but Does Not Specifically Bind any Coproantigen in Canines Infected with Roundworm or Whipworm Polyclonal antibody preparation and isolation. A polyclonal antibody anti-ASP5-1 was raised in rabbit against a polypeptide having amino acid sequence corresponding to SEQ ID NO:4 (i.e. ASP5-1) and purified from serum by using standard methods.

Briefly, nucleotides 50 through 427 of SEQ ID NO:2 were cloned in-frame into a vector (D8223, which is a derivative of pUC19) to create the plasmid D8339. Specifically, the 129 amino acids of SEQ ID NO:4 that follow the methionine residue at the N-terminus of that sequence correspond to a portion of SEQ ID NO:3 and are encoded for by the cloned portion of SEQ ID NO:2. In the D8339 plasmid, the N-terminal methionine residue was encoded for by vector sequence at the junction of that plasmid where the vector was ligated to the cloned sequence from SEQ ID NO:2.

DNA sequence encoding SEQ ID NO:2 was then cleaved from the pTDX184 plasmid by restriction exonuclease digestion (NdeI and BamHI) and purified. This purified sequence was then ligated to linearized expression vector, pET28a, and the resulting circular construct (pTDX204::DIV6716) was transformed into BL21 (DE3) *E. coli* cells. (The complete sequence of the insert was confirmed by DNA sequence analysis.) Expression of His-tagged fusion protein was induced by addition of 1 mM IPTG to cultures of the transformed *E. coli*. Recombinant protein was solubilized in 6 M urea and purified by nickel affinity and ion exchange chromatography. (This recombinant protein is hereinafter is referred to as "ASP5-1".)

After ASP5-1 protein was introduced into rabbits, anti-ASP5-1 pAB was purified from the plasma of the immunized rabbits by isolating IgG antibody by protein G affinity chromatography.

Canine fecal extract preparation. Canine animals known to be free of parasitic worm infection or to be infected with one of either hookworm (*Ancylostoma caninum, Uncinavia*), roundworm (*Toxocara canis*), whipworm (*Trichuris vulpis*) or heartworm (*Dirofilaria immitis*) provided the source of fecal samples. Fecal extract was generated from these canine samples as described above.

ELISA assays. Purified anti-ASP5-1 pAB (3 µg/ml in each well) was immobilized by physical adsorption on Immulon 1B 96-well plates overnight at 4° C. The plates were then blocked with 1% BSA in 0.1M Tris pH 7.0 at 4° C. overnight, followed by drying at room temperature. Approximately 100 µl of fecal extract was added to each well and allowed to incubate at room temperature for one hour. The wells were then washed five times with a PBS-Tween-20 solution according to standard methods known to those of ordinary skill in the art. In a separate reaction vessel, free anti-ASP5-1 pAB was labeled with horseradish peroxidase (HRP) by using the crosslinker succinimidyl 4-[N-maleimidomethyl]cyclohexane-1-carboxylate (SMCC) to create a conjugate, and 10 µg/ml of this conjugate was added to each well having immobilized anti-DIV6716 pAB. Following a 30-minute incubation period at room temperature, unbound conjugate was washed from the wells by using. PBS-Tweeze-20 solution according to standard methods known to those of ordinary skill in the art. 50 µl of TMBLUE® peroxidase substrate (SeraCare Life Sciences, West Bridgewater, Mass.) was then added to each well and the plates were incubated for 10 minutes at room temperature. After stopping each enzymatic reaction with 0.1% sodium dodecyl sulfate (SDS) following the 10-minute incubation period, the optical density (OD) value of each well of the 96-well plate was measured at A650 by standard spectrophotometric techniques by using an ELISA plate reader to generate an "OD650 value" (or, more simply, an "OD value") for each well. In this arrangement, the OD value obtained for any particular well of the 96-well plate was directly proportional to the amount of specifically bound antigen present in the well.

It was a goal of Example 2 to determine whether the polyclonal antibody anti-ASP5-1 specifically binds hookworm in fecal extract. Single OD determinations for pooled canine fecal samples obtained in Example 1 are shown in FIG. 2. These fecal samples were obtained from 5 canine animals known to be free of parasitic worm infection ("Uninfected"), 5 canine animals known to be infected with hookworm ("Hookworm-infected"), 5 canine animals known to be infected with roundworm ("Roundworm-infected") and 5 canine animals known to be infected with whipworm ("Whipworm-infected"). (Specifically, fecal samples were obtained on post-infection day 7 for each of the five parasitic worm-infected canines.)

An OD determination also was made for a sample that included 100 µl of PBS instead of fecal extract. This PBS sample and the "uninfected" sample described above served as a negative controls. Furthermore, an OD determination also was made for a sample that contained ASP5-1 protein (SEQ ID NO:4) (added to the plate at 1 µg/ml), which served as a positive control.

Figure 3:
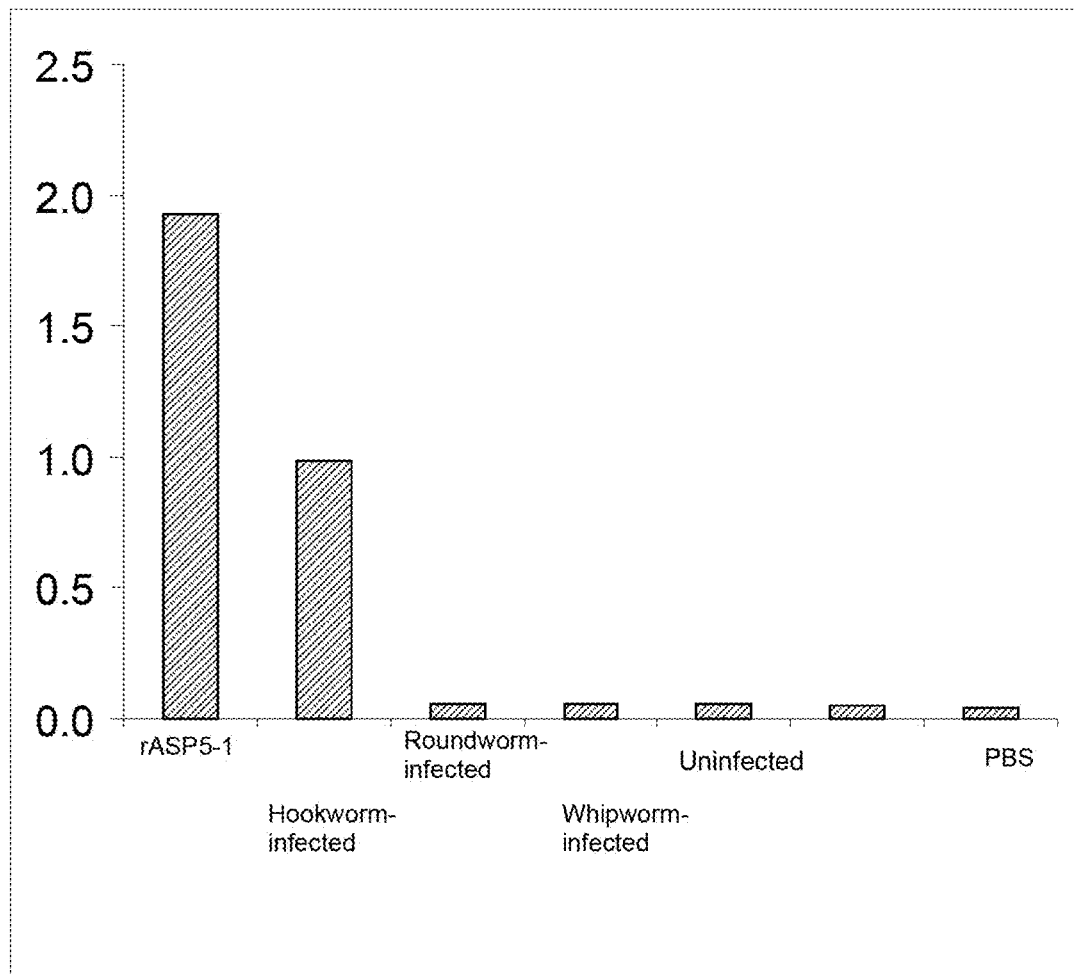
FIG. 3 shows single OD determinations for pooled canine fecal samples to show specificity of the anti-ASP5-1 pAB for hookworm.

As shown in FIG. 3, the OD value measured of each one of the uninfected and the PBS negative controls was 0.05. Conversely, the OD measured of the hookworm-infected fecal sample was 0.99, which was about 20-fold higher than was the OD values measured for negative control samples. These data indicate that anti-ASP5-1 pAB specifically binds coproantigen in hookworm-infected canine animals, but does not specifically bind any coproantigen in uninfected canine animals. These data therefore indicate that anti ASP5-1 can be used to detect the presence or absence of hookworm infection in a canine animal.

Furthermore, the OD value measured of each one of the roundworm-infected and the whipworm-infected negative controls was 0.06, which approximated the OD value measured of the negative controls. These data indicate that anti-ASP5-1 pAB does not specifically bind any roundworm or whipworm coproantigen.

Example 3

Anti-ASP5-1 pAB Detects Hookworm Coproantigen in Some Canines as Early as 9 Days After Being Infected with Hookworm. Anti-ASP5-1 pAB Does Not Detect Hookworm in Feces of Canine Animals That Have Had a Hookworm Infection, but That Have Been Dewormed It was a goal of Example 3 to determine whether anti-ASP5 pAB can detect hookworm coproantigen in hookworm-infected canines before hookworm ova first appear in the feces of those canines. It was another goal of Example 3 to determine whether anti-ASP5 pAB detects hookworm in feces of canine animals that have been rid of a prior hookworm infection.

Figure 4:
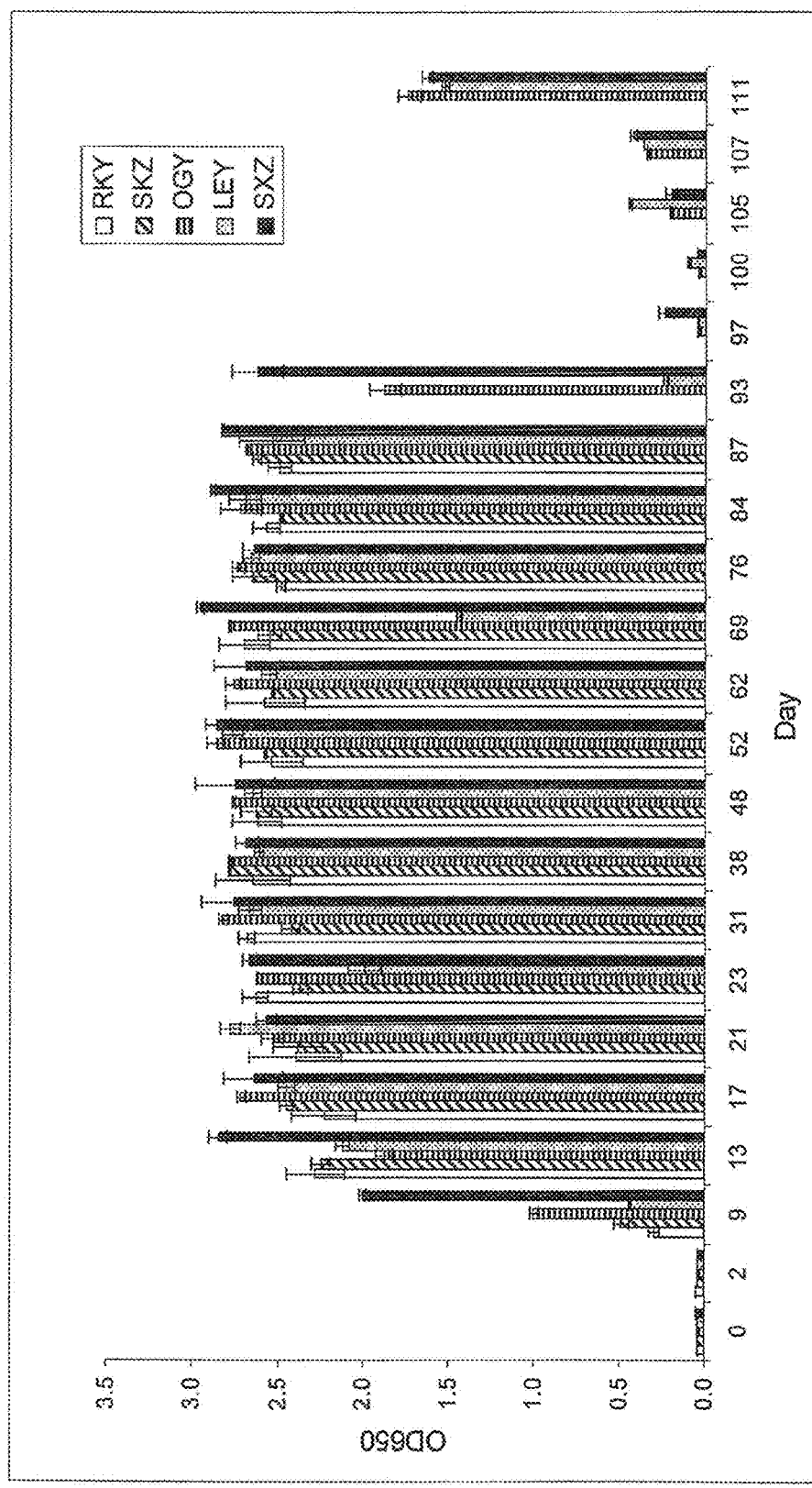
FIG. 4 shows single OD determinations of anti-ASP5-1 pAB over a period of 111 days for canines infected with hookworm.

Toward these goals, OD values were measured for fecal samples Obtained from a first set of five canines and are shown in FIG. 4. These canines, which are identified as "RKY", "SKZ", OGY", "LEY" and "SKZ", were infected with hookworm on day 0 and were treated with the Interceptor® anthelmintic agent on day 91 after the administration of the infection as described before. Fecal samples were taken from all or some of these canines on day 0, on day 2 and day 111 following the administration of the roundworm infections to these animals, and on selected days between day 2 and day 111.

Microscopic observation of the fecal samples from the first set of canines confirmed that each one of the samples taken at day 0 through day 13 and at day 97 through day 111 was substantially free of hookworm ova, and that such ova were present only in the samples at each one of days 17 through 93.

OD values, which are shown in FIG. 4 were also measured for a second set of canines, which are identified as "LCZ", "SBY", "RCZ", "SVY", and "TIY" that were never infected with hookworm (and therefore served as negative controls). Fecal samples were taken from each one of these canines on the day that the first set of canines were infected with hookworm (day 0). Furthermore, fecal sample were taken from these second set of canines on day 2 and day 107 following the administration of the roundworm infections to the first set of canines, and on selected days between day 1 and day 107. Microscopic observation of the fecal samples from the second set of canines confirmed that each one of the samples taken at day 0 through day 107 was free of roundworm ova.

Referring to FIG. 4, the average OD value measured for the first set of five canines at day 9 was 0.84, which was more than 20 times higher than was the average of the OD values (0.04) that were measured for those canines at day 0 and was about 17 times higher than was the average of the OD values (0.05) that were measured for the second set of canines (i.e., the negative control canines) at days 0 through 107. These data indicate that anti-ASP5-1 pAB is useful for detecting hookworm in feces from a hookworm-infected canine as early as 9 days after the canine first became infected with hookworm.

TABLE 1

| Canine ID | Day | | | | | | | | | | |
|---|---|---|---|---|---|---|---|---|---|---|---|
| | 0 | 2 | 9 | 13 | 17 | 21 | 23 | 31 | 38 | 48 | 52 |
| RKY | 0.04 | 0.05 | 0.29 | 2.28 | 2.23 | 2.40 | 2.63 | 2.68 | 2.65 | 2.62 | 2.53 |
| | 0.00 | 0.00 | 0.03 | 0.17 | 0.19 | 0.27 | 0.07 | 0.05 | 0.22 | 0.14 | 0.18 |
| SKZ | 0.04 | 0.04 | 0.49 | 2.25 | 2.45 | 2.38 | 2.37 | 2.43 | 2.78 | 2.62 | 2.58 |
| | 0.00 | 0.00 | 0.04 | 0.05 | 0.04 | 0.15 | 0.05 | 0.06 | 0.01 | 0.09 | 0.01 |
| OGY | 0.04 | 0.04 | 1.00 | 1.87 | 2.71 | 2.53 | 2.62 | 2.82 | 2.78 | 2.76 | 2.85 |
| | 0.00 | 0.00 | 0.02 | 0.05 | 0.03 | 0.07 | 0.00 | 0.02 | 0.01 | 0.01 | 0.05 |
| LEY | 0.04 | 0.04 | 0.44 | 2.12 | 2.45 | 2.78 | 1.99 | 2.67 | 2.61 | 2.65 | 2.77 |
| | 0.00 | 0.00 | 0.00 | 0.04 | 0.05 | 0.06 | 0.10 | 0.06 | 0.03 | 0.05 | 0.06 |

TABLE 1-continued

| Canine ID | | | | | Day | | | | | | |
|---|---|---|---|---|---|---|---|---|---|---|---|
| SXZ | 0.05 | 0.04 | 2.00 | 2.85 | 2.64 | 2.57 | 2.67 | 2.75 | 2.68 | 2.75 | 2.85 |
|  | 0.00 | 0.00 | 0.02 | 0.06 | 0.17 | 0.06 | 0.04 | 0.19 | 0.06 | 0.23 | 0.07 |

| Canine ID | 62 | 69 | 76 | 84 | 87 | 93 | 97 | 100 | 105 | 107 | 111 |
|---|---|---|---|---|---|---|---|---|---|---|---|
| RKY | 2.58 | 2.70 | 2.48 | 2.57 | 2.49 | | | | | | |
|  | 0.23 | 0.14 | 0.03 | 0.08 | 0.07 | | | | | | |
| SKZ | 2.53 | 2.55 | 2.64 | 2.48 | 2.62 | | | | | | |
|  | 0.01 | 0.07 | 0.12 | 0.01 | 0.03 | | | | | | |
| OGY | 2.76 | 2.78 | 2.73 | 2.72 | 2.67 | 1.87 | 0.04 | 0.04 | 0.20 | 0.33 | 1.73 |
|  | 0.04 | 0.01 | 0.03 | 0.12 | 0.02 | 0.09 | 0.00 | 0.00 | 0.00 | 0.01 | 0.06 |
| LEY | 2.55 | 1.43 | 2.65 | 2.69 | 2.53 | 0.23 | 0.05 | 0.10 | 0.44 | 0.36 | 1.52 |
|  | 0.05 | 0.02 | 0.05 | 0.09 | 0.19 | 0.01 | 0.00 | 0.01 | 0.01 | 0.00 | 0.02 |
| SXZ | 2.69 | 2.95 | 2.64 | 2.88 | 2.82 | 2.62 | 0.23 | 0.05 | 0.20 | 0.42 | 1.62 |
|  | 0.19 | 0.02 | 0.07 | 0.02 | 0.00 | 0.15 | 0.04 | 0.00 | 0.04 | 0.02 | 0.03 |

Table 1 contains a numerical representation of the data shown in FIG. 4. The OD values (bold) are the average of two measurement. The standard deviation is given in normal font below each average OD. For days 93-111 there is no data for canines RKY and SKZ, because they were sacrificed for necroscopic analysis.

With continuing reference to FIG. 4, the OD values measured for the fecal samples taken from the first set of five canines at days 38 through 93 were many times higher than were the OD values measured for fecal samples from those same canines following their treatment with the anthelmintic agent. These data indicate that anti-ASP5-1 pAB does not detect hookworm in feces from a canine that has been rid of a prior hookworm infection. In samples taken from the first set of five canines at days 105 through 111, the OD values increase again. The anthelmintic used, Interceptor®, is shown not to be 100% effective upon a single dose. Signal is regained as nematodes recover. In addition, Interceptor may not kill all larval stages; therefore, any larvae present in the patient would give rise to new adult worms.

Example 4

Anti-ASP5-1 pAB detects hookworm coproantigen from *Uncinaria stenocephala* in some canines as early as 15 days after being infected with hookworm, and anti-ASP5-1 pAB does not detect hookworm in feces of canine animals that have had a hookworm infection, but that have been dewormed.

It was a goal of Example 4 to determine whether anti-ASP5-1 pAB can detect hookworm coproantigen from *Uncinaria stenocephala* in hookworm-infected canines. It was another goal of Example 4 to determine whether anti-ASP5-1 pAB detects the hookworm species *Uncinaria stenocephala* in feces of canine animals that have been rid of a prior hookworm infection.

Figure 5:
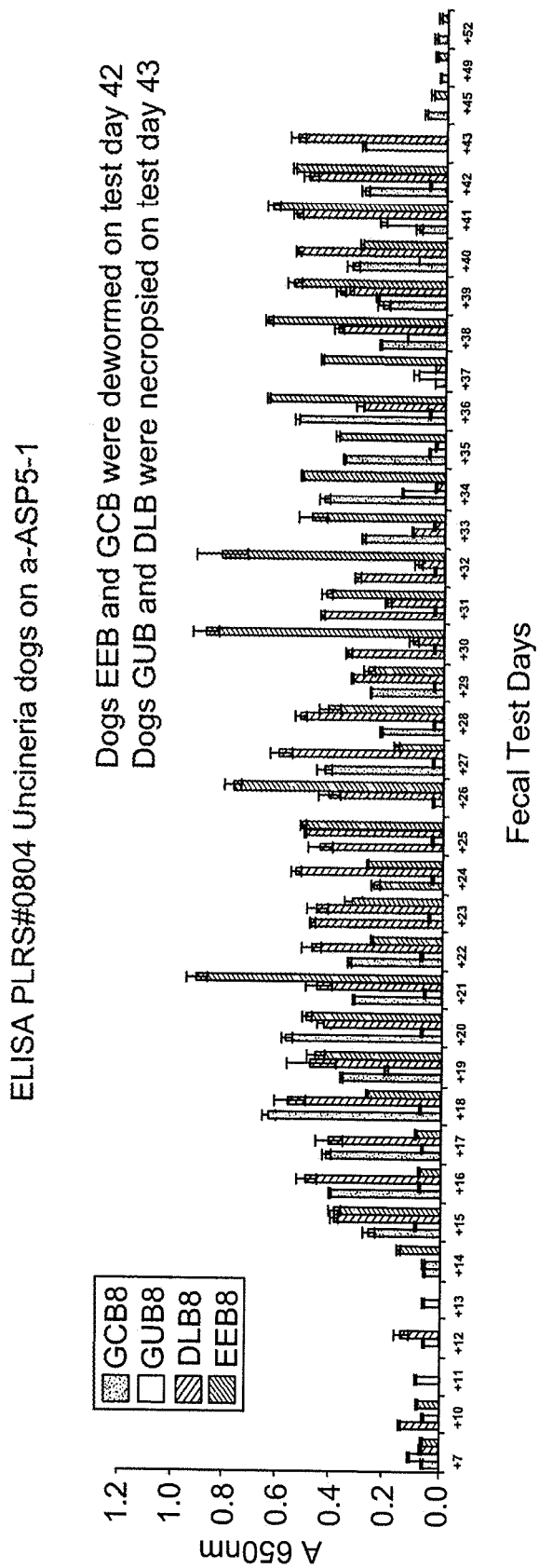
FIG. 5 shows single OD determinations of anti-ASP5-1 pAB over a period of 52 days for canines infected with *Uncinaria stenocephala* hookworm.

Toward these goals, OD values were measured for fecal samples obtained from a set of four canines and are shown in FIG. 5. These canines, which are identified as "GCB8", "GUB8", "DLB8", and "EEB8", were infected with hookworm species *Uncinaria stenocephala* on day 0 and were treated with the Interceptor® anthelmintic agent on day 42 after the administration of the infection as described before. Fecal samples were taken from all or some of these canines on selected days between day 7 and day 52 following the administration of the hookworm infections to these animals. Microscopic observation of the fecal samples from the canines confirmed that hookworm ova were detected as early as day 8 (GUB8) to day 21 (EEB8), and that by day 49, all samples were free of ova for the remainder of the study (Table 2).

Referring to FIG. 5, the average OD value measured for the set of four canines at day 15 was 0.28, which was more than 4.4 times higher than was the average of the OD values (0.06) that were measured for those canines at day 7 and was about 6.5 times higher than was the average of the OD values (0.04) that were measured for a second set of canines (i.e., the negative control canines, data not shown) at days 35 through 124 These data indicate that anti-ASP5-1 pAB is useful for detecting *Uncinaria stenocephala* hookworm in feces from an *Uncinaria stenocephala* hookworm-infected canine as early as 15 days after the canine first became infected with *Uncinaria stenocephala* hookworm.

TABLE 2

Eggs per grain feces data for *U. stenocephala* infected dogs from PLRS

| Canine ID | Day | | | | | | | | | | | | | | | | | | | | |
|---|---|---|---|---|---|---|---|---|---|---|---|---|---|---|---|---|---|---|---|---|---|
|  | 8 | 12 | 14 | 15 | 17 | 19 | 21 | 22 | 24 | 26 | 29 | 30 | 33 | 35 | 36 | 38 | 42 | 43 | 45 | 49 | 52 |
| DLB8 | 0 | 0 |  | 0 |  | 6 |  | 57 |  | 121 | 174 |  | 407 |  | 215 |  | 419 |  |  |  |  |
| GUB8 | 13 | 3 |  | 4 |  | 0 |  | 2 |  | 7 | 3 |  | 15 |  | 6 |  |  | 27 |  |  |  |
| EEB8 |  |  | 0 |  | 0 |  | 14 |  | 46 |  |  | 27 |  | 54 |  | 402 | 65 |  | 0 | 0 | 0 |
| GCB8 |  |  |  | 30 |  | 177 |  | 742 |  | 452 |  |  | 376 |  | 326 |  | 112 | 550 |  | 1 | 0 | 0 |

With continuing reference to FIG. 5, the OD values measured for the fecal samples taken from the set of four canines at days 15 through 42 were many times higher than were the OD values measured for fecal samples from those same canines following their treatment with the anthelmintic agent. OD values returned to background by day 45. These data indicate that anti ASP5-1 pAB does not detect *Uncinaria stenocephala* hookworm in feces from a canine that has been rid of a prior hookworm infection.

the negative control felines; data not shown) at days +38 through +105 These data indicate that anti-ASP5-1 pAB is useful for detecting *Ancylostoma tubaeforme* hookworm in feces from an *Ancylostoma tubaeforme* hookworm-infected feline as early as 14 days after the feline first became infected with *Ancylostoma tubaeforme* hookworm.

TABLE 3

Eggs per gram feces data for *A. tubaeforme* infected felines from PLRS
Days post infection

| Feline ID | +21 | +28 | +30 | +35 | +38 | +42 | +45 | +49 | +52 | +57 | +59 |
|---|---|---|---|---|---|---|---|---|---|---|---|
| AAA3 | 39 | 272 | 1035 | 514 | 954 | 1028 | 210 | 0 | 0 | 0 | 0 |
| AQU3 | 11 | 237 | 391 | 480 | 601 | 730 | 481 | | | | |
| JAD1 | 96 | 589 | 735 | 577 | 749 | 415 | 502 | 0 | 0 | 0 | 0 |
| AQU5 | 0 | 0 | 5 | 192 | 92 | 791 | 239 | 175 | 321 | 194 | 77 |

Example 5

Anti-ASP5-1 pAB detects hookworm coproantigen from *Ancylostoma tubaeforme* in some felines as early as 14 days after being infected with hookworm, and anti-ASP5-1 pAB does not detect hookworm in feces of feline animals that have had a hookworm infection, but that have been dewormed.

It was a goal of Example 5 to determine whether anti-ASP5-1 pAB can detect hookworm coproantigen from *Ancylostoma tubaeforme* in hookworm-infected felines before hookworm ova first appear in the feces of those felines. It was another goal of Example 4 to determine whether anti-ASP5-1 pAB detects the hookworm species *Ancylostoma tubaeforme* in feces of feline animals that have been rid of a prior hookworm infection.

Figure 6:
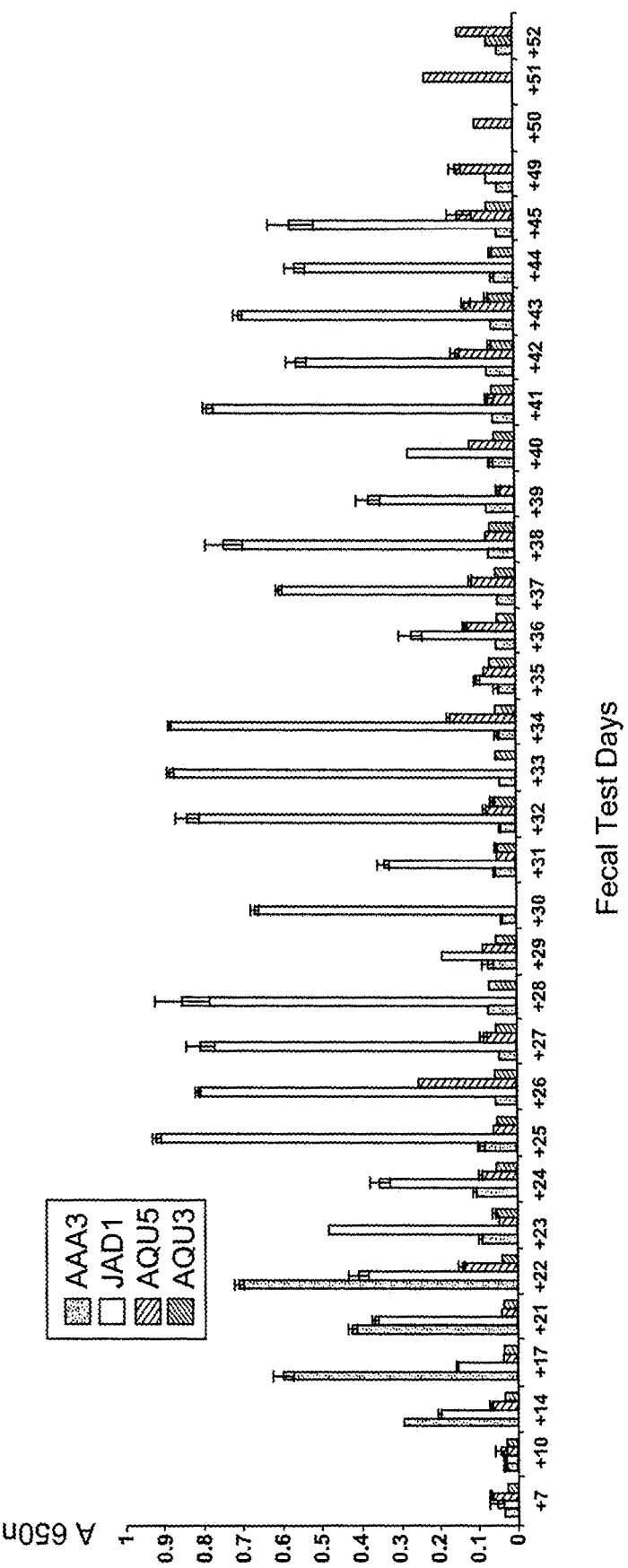
FIG. 6 shows single OD determinations of anti-ASP5-1 pAB over a period of 52 days for felines infected with *Ancylostoma tubaeforme* hookworm.

Toward these goals, OD values were measured for fecal samples obtained from a set of four felines and are shown in FIG. 6. These felines, which are identified as "AAA3", "JAD1", "AQU5", and "AQU3", were infected with hookworm species *Ancylostoma tubaeforme* on day 0 and were treated with the Interceptor® anthelmintic agent on day 49 after the administration of the infection as described before. Fecal samples were taken from all or some of these felines on day −14, on day +7 and day 73 following the administration of the hookworm infections to these animals, and on selected days between day +7 and day +59. Microscopic observation of the fecal samples from the felines confirmed that each one of the samples taken at day −14 through day +17 and at day +49 through day +73 was substantially free of hookworm ova, and that such ova were present only in the samples at each one of days 21 through 45 (Table 3).

Referring to FIG. 6, the average OD value measured for the set of four felines at day +14 was 0.15, which was more than 3 times higher than was the average of the OD values (0.05) that were measured for those felines at day 7 and was about 3 times higher than was the average of the OD values (0.05) that were measured for the second set of felines (i.e., With continuing reference to FIG. 6, the average OD values measured for the fecal samples taken from the set of four felines at days +14 through +45 were many times higher than were the OD values measured for fecal samples from those same felines following their treatment with the anthelmintic agent. These data indicate that anti-ASP5-1 pAB does not detect *Ancylostoma tubaeforme* hookworm in feces from a feline that has been rid of a prior hookworm infection. The anthelmintic used, Interceptor®, is known not to be 100% effective upon a single dose. Signal is retained as nematodes recover. In addition, Interceptor may not kill all larval stages; therefore, any larvae present in the patient would give rise to new adult worms.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

A number of examples to help illustrate the invention have been described. Nevertheless, it will be understood that various modifications may be made without departing from the spirit and scope of the invention. Accordingly, other embodiments are within the scope of the claims appended hereto.

What is claimed is:

1. A method of diagnosing and treating an intestinal hookworm infection in a mammal, the method comprising the steps of:
   (a) obtaining a fecal sample from the mammal;
   (b) contacting the sample from the mammal with one or more antibodies that can specifically bind to CoproASP5;
   (c) detecting the presence or absence of the one or more hookworm coproantigens or detecting the presence or absence of one or more complexes that include the one or more hookworm coproantigens and the one or more antibodies using a labeled secondary antibody;
   (d) diagnosing the mammal as having or as not having the hookworm infection based on the detection of the presence or absence of the one or more hookworm coproantigens or the one or more complexes; and
   (e) administering an anti-helminthic agent to treat the mammal having the hookworm infection.

2. The method of claim 1, wherein the one or more antibodies are obtained by immunization with a polypeptide of amino acid sequence SEQ ID NO:4, or an antigenic portion thereof.

3. The method of claim 2, wherein the amino acid sequence of the polypeptide has 30 or fewer conserved amino acid substitutions to SEQ ID NO:4.

4. The method of claim 3, wherein the amino acid sequence of the polypeptide is a conservative variant of SEQ ID NO:4.

5. The method of claim 1, wherein the mammal is a canine or a feline.

6. The method of claim 1, wherein the hookworm is *Ancylostoma caninum* or *Ancylostoma braziliense*.

7. The method of claim 1, wherein one or more of the one or more antibodies are labeled.

8. The method of claim 1, wherein the one or more antibodies are immobilized on a solid support.

9. The method of claim 8, wherein the solid support forms part of an enzyme-linked immunosorbent assay device.

10. The method of claim 9, wherein the enzyme-linked immunosorbent assay device is a lateral flow immunoassay device.

11. The method according to claim 1, wherein the CoproASP5 is an N-terminal ASP-5 fragment of about 28 kDa.

12. The method of claim 1, wherein subsequent to step (e), further comprising repeating steps (a) to (d).

\* \* \* \* \*

SEQUENCE LISTING

<160> NUMBER OF SEQ ID NOS: 9

<210> SEQ ID NO 1
<211> LENGTH: 1343
<212> TYPE: DNA
<213> ORGANISM: Ancylostoma

<400> SEQUENCE: 1

| | | | | | |
|---|---|---|---|---|---|
| atgggcagca | gccatcatca | tcatcatcac | agcagcggcc | tggtgccgcg | cggcagccat | 60 |
| atggctagca | tgactggtgg | acagcaaatg | ggtcgcggat | ccgaattcga | gctcaccact | 120 |
| tgtccaggaa | atgatctaac | agatgctgaa | cgcacactgc | taactagggt | gcacaattcc | 180 |
| attcgacggg | aaatagcgca | aggagttgca | acaactacc | atggtggtaa | actgcctgct | 240 |
| ggaaagaaca | tatacaggat | gagatacagc | tgtgagctgg | aacaggctgc | tattgatgct | 300 |
| agtcaaacct | tctgttccgc | atcattggag | gaaccacaga | aatatggaca | aaacatccaa | 360 |
| gcatacgtca | caccatctat | aatcgctcgc | ccgaaaaacg | accttcttga | agatgcagtg | 420 |
| aaacaatggt | atctgcctgt | tatctactac | ggccaacgcg | acgcggccaa | caagttcacc | 480 |
| gatccgcgct | tgtacacatt | tgcaaacctc | gcctacgaca | gaacactgc | acttggctgt | 540 |
| cactatgcga | atgtcaagg | ccctgacaga | atcgtcatta | gttgcatgta | caacaacgtc | 600 |
| gttcctgaca | cgctgtgat | ctacgagcca | ggaactgctt | gcgtaaaaga | tcaggactgc | 660 |
| actacttatc | ctcagtccac | atgcaaggac | agcctttgca | ttattcctac | gccacatcca | 720 |
| ccaaatccac | caaatccacc | acctgcaatg | tgtccaaacg | ctgaaatgac | tgatgcagca | 780 |
| cgaaagaagg | tcctcgacat | gcacaactgg | cgcagatcgc | agctcgctct | gggaaacgtt | 840 |
| caaaacggga | aaaatgctta | caactgcccc | actgcaacag | acatgtacaa | gatggaatat | 900 |
| gattgcgacc | tcgagaacag | cgctctagcg | tatgcaaagc | aatgtagtct | cgttggttca | 960 |
| gcagaaggaa | ctcgtccagg | agaaggcgag | aatgtccaca | aaggcgctct | cgtaaccgat | 1020 |
| ccggaggctg | cagttcagac | cgcagttcaa | gcatggtgga | gtcaaatctc | acaaaatgga | 1080 |
| ctcaatgcac | agatgaaatt | cactgctttc | ttgaaggaca | agcctgacgc | tccgacagcg | 1140 |
| tttacacaga | tggcgtgggc | caaatccgta | aagcttggat | gtgctgtctc | taattgtcag | 1200 |
| gcagataccct | tcaccgtctg | tagatacaaa | gctgccggaa | acatcgtggg | cgaattcatc | 1260 |
| tataccaagg | gaaatgtatg | cgacgcctgt | aaagccacat | gcattaccgc | ggaaggtctt | 1320 |
| tgcccaacgc | cttgagcggc | cgc | | | | 1343 |

<210> SEQ ID NO 2
<211> LENGTH: 767
<212> TYPE: DNA
<213> ORGANISM: Ancylostoma

<400> SEQUENCE: 2

| | | | | | |
|---|---|---|---|---|---|
| atgggcagca | gccatcatca | tcatcatcac | agcagcggcc | tggtgccgcg | cggcagccat | 60 |
| atggctagca | tgactggtgg | acagcaaatg | ggtcgcggat | ccgaattcga | gctcaccact | 120 |
| tgtccaggaa | atgatctaac | agatgctgaa | cgcacactgc | taactagggt | gcacaattcc | 180 |
| attcgacggg | aaatagcgca | aggagttgca | acaactacc | atggtggtaa | actgcctgct | 240 |
| ggaaagaaca | tatacaggat | gagatacagc | tgtgagctgg | aacaggctgc | tattgatgct | 300 |
| agtcaaacct | tctgttccgc | atcattggag | gaaccacaga | aatatggaca | aaacatccaa | 360 |
| gcatacgtca | caccatctat | aatcgctcgc | ccgaaaaacg | accttcttga | agatgcagtg | 420 |
| aaacaatggt | atctgcctgt | tatctactac | ggccagcgcg | acgcggccaa | caagtttacg | 480 |

-continued

```
gatccgcgct tgtacacatt tgcaaacctc gcctacgaca agaacactgc acttggctgt    540
cactatgcga aatgtcaagg ccctgacaga atcgtcatta gttgcatgta caacaacgtc    600
gttcctgaca acgcagtgat ctacgagcct ggaactgctt gcgtaaaaga tgcggactgc    660
actacttatc ctcagtccac atgcaaggac agcctttgca ttattcctac gccacatcca    720
ccaaatccac caaatccacc accagcaatg agtccatgag cggccgc                  767
```

```
<210> SEQ ID NO 3
<211> LENGTH: 444
<212> TYPE: PRT
<213> ORGANISM: Ancylostoma

<400> SEQUENCE: 3
```

Met Gly Ser Ser His His His His His Ser Gly Leu Val Pro
1               5                   10                  15

Arg Gly Ser His Met Ala Ser Met Thr Gly Gly Gln Gln Met Gly Arg
            20                  25                  30

Gly Ser Glu Phe Glu Leu Thr Thr Cys Pro Gly Asn Asp Leu Thr Asp
        35                  40                  45

Ala Glu Arg Thr Leu Leu Thr Arg Val His Asn Ser Ile Arg Arg Glu
    50                  55                  60

Ile Ala Gln Gly Val Ala Asn Asn Tyr His Gly Gly Lys Leu Pro Ala
65                  70                  75                  80

Gly Lys Asn Ile Tyr Arg Met Arg Tyr Ser Cys Glu Leu Glu Gln Ala
                85                  90                  95

Ala Ile Asp Ala Ser Gln Thr Phe Cys Ser Ala Ser Leu Glu Glu Pro
            100                 105                 110

Gln Lys Tyr Gly Gln Asn Ile Gln Ala Tyr Val Thr Pro Ser Ile Ile
        115                 120                 125

Ala Arg Pro Lys Asn Asp Leu Leu Glu Asp Ala Val Lys Gln Trp Tyr
    130                 135                 140

Leu Pro Val Ile Tyr Tyr Gly Gln Arg Asp Ala Ala Asn Lys Phe Thr
145                 150                 155                 160

Asp Pro Arg Leu Tyr Thr Phe Ala Asn Leu Ala Tyr Asp Lys Asn Thr
                165                 170                 175

Ala Leu Gly Cys His Tyr Ala Lys Cys Gln Gly Pro Asp Arg Ile Val
            180                 185                 190

Ile Ser Cys Met Tyr Asn Asn Val Val Pro Asp Asn Ala Val Ile Tyr
        195                 200                 205

Glu Pro Gly Thr Ala Cys Val Lys Asp Gln Asp Cys Thr Thr Tyr Pro
    210                 215                 220

Gln Ser Thr Cys Lys Asp Ser Leu Cys Ile Ile Pro Thr Pro His Pro
225                 230                 235                 240

Pro Asn Pro Pro Asn Pro Pro Ala Met Cys Pro Asn Ala Glu Met
                245                 250                 255

Thr Asp Ala Ala Arg Lys Lys Val Leu Asp Met His Asn Trp Arg Arg
            260                 265                 270

Ser Gln Leu Ala Leu Gly Asn Val Gln Asn Gly Lys Asn Ala Tyr Asn
        275                 280                 285

Cys Pro Thr Ala Thr Asp Met Tyr Lys Met Glu Tyr Asp Cys Asp Leu
    290                 295                 300

Glu Asn Ser Ala Leu Ala Tyr Ala Lys Gln Cys Ser Leu Val Gly Ser
305                 310                 315                 320

```
Ala Glu Gly Thr Arg Pro Gly Glu Gly Glu Asn Val His Lys Gly Ala
            325                 330                 335

Leu Val Thr Asp Pro Glu Ala Val Gln Thr Ala Val Gln Ala Trp
            340                 345                 350

Trp Ser Gln Ile Ser Gln Asn Gly Leu Asn Ala Gln Met Lys Phe Thr
            355                 360                 365

Ala Phe Leu Lys Asp Lys Pro Asp Ala Pro Thr Ala Phe Thr Gln Met
            370                 375                 380

Ala Trp Ala Lys Ser Val Lys Leu Gly Cys Ala Val Ser Asn Cys Gln
385                 390                 395                 400

Ala Asp Thr Phe Thr Val Cys Arg Tyr Lys Ala Ala Gly Asn Ile Val
            405                 410                 415

Gly Glu Phe Ile Tyr Thr Lys Gly Asn Val Cys Asp Ala Cys Lys Ala
            420                 425                 430

Thr Cys Ile Thr Ala Glu Gly Leu Cys Pro Thr Pro
            435                 440

<210> SEQ ID NO 4
<211> LENGTH: 252
<212> TYPE: PRT
<213> ORGANISM: Ancylostoma

<400> SEQUENCE: 4

Met Gly Ser Ser His His His His His Ser Ser Gly Leu Val Pro
1               5                   10                  15

Arg Gly Ser His Met Ala Ser Met Thr Gly Gly Gln Gln Met Gly Arg
            20                  25                  30

Gly Ser Glu Phe Glu Leu Thr Thr Cys Pro Gly Asn Asp Leu Thr Asp
            35                  40                  45

Ala Glu Arg Thr Leu Leu Thr Arg Val His Asn Ser Ile Arg Arg Glu
        50                  55                  60

Ile Ala Gln Gly Val Ala Asn Asn Tyr His Gly Gly Lys Leu Pro Ala
65                  70                  75                  80

Gly Lys Asn Ile Tyr Arg Met Arg Tyr Ser Cys Glu Leu Glu Gln Ala
            85                  90                  95

Ala Ile Asp Ala Ser Gln Thr Phe Cys Ser Ala Ser Leu Glu Glu Pro
            100                 105                 110

Gln Lys Tyr Gly Gln Asn Ile Gln Ala Tyr Val Thr Pro Ser Ile Ile
            115                 120                 125

Ala Arg Pro Lys Asn Asp Leu Leu Glu Asp Ala Val Lys Gln Trp Tyr
            130                 135                 140

Leu Pro Val Ile Tyr Tyr Gly Gln Arg Asp Ala Ala Asn Lys Phe Thr
145                 150                 155                 160

Asp Pro Arg Leu Tyr Thr Phe Ala Asn Leu Ala Tyr Asp Lys Asn Thr
            165                 170                 175

Ala Leu Gly Cys His Tyr Ala Lys Cys Gln Gly Pro Asp Arg Ile Val
            180                 185                 190

Ile Ser Cys Met Tyr Asn Asn Val Val Pro Asp Asn Ala Val Ile Tyr
            195                 200                 205

Glu Pro Gly Thr Ala Cys Val Lys Asp Ala Asp Cys Thr Thr Tyr Pro
            210                 215                 220

Gln Ser Thr Cys Lys Asp Ser Leu Cys Ile Ile Pro Thr Pro His Pro
225                 230                 235                 240

Pro Asn Pro Pro Asn Pro Pro Ala Met Ser Pro
            245                 250
```

<210> SEQ ID NO 5
<211> LENGTH: 424
<212> TYPE: PRT
<213> ORGANISM: Ancylostoma

<400> SEQUENCE: 5

```
Met Pro Asn Leu Leu Leu Leu Phe Leu Ser Leu Pro Gly Ala Ile
1               5                   10                  15

Leu Ser Thr Thr Cys Pro Gly Asn Asp Leu Thr Asp Ala Glu Arg Thr
                20                  25                  30

Leu Leu Thr Arg Val His Asn Ser Ile Arg Arg Glu Ile Ala Gln Gly
            35                  40                  45

Val Ala Asn Asn Tyr His Gly Gly Lys Leu Pro Ala Gly Lys Asn Ile
    50                  55                  60

Tyr Arg Met Arg Tyr Ser Cys Glu Leu Glu Gln Ala Ala Ile Asp Ala
65                  70                  75                  80

Ser Gln Thr Phe Cys Ser Ala Ser Leu Glu Glu Pro Gln Lys Tyr Gly
                85                  90                  95

Gln Asn Ile Gln Ala Tyr Val Thr Pro Ser Ile Ile Ala Arg Pro Lys
            100                 105                 110

Asn Asp Leu Leu Glu Asp Ala Val Lys Gln Trp Tyr Leu Pro Val Ile
            115                 120                 125

Tyr Tyr Gly Gln Arg Asp Ala Ala Asn Lys Phe Thr Asp Pro Arg Leu
            130                 135                 140

Tyr Thr Phe Ala Asn Leu Ala Tyr Asp Lys Asn Thr Ala Leu Gly Cys
145                 150                 155                 160

His Tyr Ala Lys Cys Gln Gly Pro Asp Arg Ile Val Ile Ser Cys Met
                165                 170                 175

Tyr Asn Asn Val Val Pro Asp Asn Ala Val Ile Tyr Glu Pro Gly Thr
            180                 185                 190

Ala Cys Val Lys Asp Ala Asp Cys Thr Thr Tyr Pro Gln Ser Thr Cys
            195                 200                 205

Lys Asp Ser Leu Cys Ile Ile Pro Thr His Pro Pro Asn Pro Pro
210                 215                 220

Asn Pro Pro Pro Ala Met Ser Pro Asn Ala Glu Met Thr Asp Ala Ala
225                 230                 235                 240

Arg Lys Lys Val Leu Gly Met His Asn Trp Arg Arg Ser Gln Val Ala
                245                 250                 255

Leu Gly Asn Val Gln Asn Gly Lys Asn Ala Tyr Asn Cys Pro Thr Ala
            260                 265                 270

Thr Asp Met Tyr Lys Ile Glu Tyr Asp Cys Asp Leu Glu Asn Ser Ala
            275                 280                 285

Leu Ala Tyr Ala Lys Gln Cys Ser Leu Val Gly Ser Ala Glu Gly Thr
    290                 295                 300

Arg Pro Gly Glu Gly Glu Asn Val His Lys Gly Ala Leu Val Thr Asp
305                 310                 315                 320

Pro Glu Ala Ala Val Gln Thr Ala Val Gln Ala Trp Trp Ser Gln Ile
                325                 330                 335

Ser Gln Asn Gly Leu Asn Ala Gln Met Lys Phe Thr Ala Phe Leu Lys
            340                 345                 350

Asp Lys Pro Asp Ala Pro Thr Ala Phe Thr Gln Met Ala Trp Ala Lys
            355                 360                 365

Ser Val Lys Leu Gly Cys Ala Val Ser Asn Cys Gln Ala Asp Thr Phe
```

```
                   370                 375                 380
Thr Val Cys Arg Tyr Lys Ala Ala Gly Asn Ile Val Gly Glu Phe Ile
385                 390                 395                 400

Tyr Thr Lys Gly Asn Val Cys Asp Ala Cys Lys Ala Thr Cys Ile Thr
                    405                 410                 415

Ala Glu Gly Leu Cys Pro Thr Pro
                420

<210> SEQ ID NO 6
<211> LENGTH: 11
<212> TYPE: PRT
<213> ORGANISM: Artificial Sequence
<220> FEATURE:
<223> OTHER INFORMATION: MS peptide 1

<400> SEQUENCE: 6

Lys Asn Asp Leu Leu Glu Asp Ala Val Lys Gln
1               5                   10

<210> SEQ ID NO 7
<211> LENGTH: 14
<212> TYPE: PRT
<213> ORGANISM: Artificial Sequence
<220> FEATURE:
<223> OTHER INFORMATION: MS peptide 2

<400> SEQUENCE: 7

Lys Gln Trp Tyr Leu Pro Val Ile Tyr Tyr Gly Gln Arg Asp
1               5                   10

<210> SEQ ID NO 8
<211> LENGTH: 13
<212> TYPE: PRT
<213> ORGANISM: Artificial Sequence
<220> FEATURE:
<223> OTHER INFORMATION: MS peptide 3

<400> SEQUENCE: 8

Arg Leu Tyr Thr Phe Ala Asn Leu Ala Tyr Asp Lys Asn
1               5                   10

<210> SEQ ID NO 9
<211> LENGTH: 12
<212> TYPE: PRT
<213> ORGANISM: Artificial Sequence
<220> FEATURE:
<223> OTHER INFORMATION: MS peptide 4

<400> SEQUENCE: 9

Lys Asn Thr Ala Leu Gly Cys His Tyr Ala Lys Cys
1               5                   10
```